United States Patent
Hess et al.

(10) Patent No.: US 7,495,134 B2
(45) Date of Patent: Feb. 24, 2009

(54) CARBONYLATION METHOD BY ADDING SECONDARY STERICALLY HINDERED AMINES

(75) Inventors: Dieter Hess, Marl (DE); Dagmara Ortmann, Brig-Glis (CH); Oliver Moeller, Oer-Erkenschwick (DE); Klaus-Diether Wiese, Haltern am See (DE); Dirk Fridag, Haltern am See (DE); Wilfried Bueschken, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 0 days.

(21) Appl. No.: 12/065,091

(22) PCT Filed: Jun. 2, 2006

(86) PCT No.: PCT/EP2006/062872

§ 371 (c)(1),
(2), (4) Date: Feb. 28, 2008

(87) PCT Pub. No.: WO2007/028660

PCT Pub. Date: Mar. 15, 2007

(65) Prior Publication Data

US 2008/0188686 A1    Aug. 7, 2008

(30) Foreign Application Priority Data

Sep. 7, 2005    (DE)    ........................ 10 2005 042 464

(51) Int. Cl.
C07C 45/50    (2006.01)
B01J 31/00    (2006.01)

(52) U.S. Cl. ........................ 568/454; 502/167

(58) Field of Classification Search ................ 568/454; 502/167
See application file for complete search history.

(56) References Cited

U.S. PATENT DOCUMENTS

| | | | |
|---|---|---|---|
| 4,567,306 A | 1/1986 | Dennis et al. |
| 5,093,534 A | 3/1992 | Ludwig et al. |
| 5,767,321 A | 6/1998 | Billig et al. |
| 6,015,928 A | 1/2000 | Gubisch et al. |
| 6,184,424 B1 | 2/2001 | Bueschken et al. |
| 6,239,318 B1 | 5/2001 | Schuler et al. |
| 6,331,657 B1 | 12/2001 | Kaizik et al. |
| 6,403,836 B2 | 6/2002 | Kaizik et al. |
| 6,403,837 B1 | 6/2002 | Hess et al. |
| 6,407,295 B1 | 6/2002 | Kaizik et al. |
| 6,482,992 B2 | 11/2002 | Scholz et al. |
| 6,492,564 B1 | 12/2002 | Wiese et al. |
| 6,500,991 B2 | 12/2002 | Wiese et al. |
| 6,555,716 B2 | 4/2003 | Protzmann et al. |
| 6,570,033 B2 | 5/2003 | Rottger et al. |
| 6,627,782 B2 | 9/2003 | Kaizik et al. |
| 6,680,414 B2 | 1/2004 | Knoop et al. |
| 6,720,457 B2 | 4/2004 | Drees et al. |
| 6,818,770 B2 | 11/2004 | Selent et al. |
| 6,924,389 B2 | 8/2005 | Jackstell et al. |
| 6,956,133 B2 | 10/2005 | Jackstell et al. |
| 6,960,699 B2 | 11/2005 | Totsch et al. |
| 7,009,068 B2 | 3/2006 | Schmutzler et al. |
| 7,109,346 B2 | 9/2006 | Beller et al. |
| 7,138,552 B2 | 11/2006 | Kaizik et al. |
| 7,154,012 B2 | 12/2006 | Lueken et al. |
| 7,161,020 B2 | 1/2007 | Selent et al. |
| 7,179,947 B2 | 2/2007 | Lueken et al. |
| 7,193,116 B2 | 3/2007 | Moeller et al. |
| 7,217,828 B2 | 5/2007 | Selent et al. |
| 7,232,931 B2 | 6/2007 | Toetsch et al. |
| 7,317,130 B2 | 1/2008 | Moeller et al. |
| 7,323,586 B2 | 1/2008 | Wiese et al. |
| 7,342,144 B2 | 3/2008 | Kaizik et al. |
| 7,345,185 B2 | 3/2008 | Ortmann et al. |
| 2003/0144559 A1 | 7/2003 | Hess et al. |
| 2003/0195368 A1 | 10/2003 | Rottger et al. |
| 2004/0242947 A1 | 12/2004 | Beller et al. |
| 2005/0171371 A1 | 8/2005 | Borner et al. |
| 2005/0209455 A1 | 9/2005 | Boerner et al. |
| 2005/0256281 A1 | 11/2005 | Grund et al. |
| 2006/0089469 A1 | 4/2006 | Komarov et al. |
| 2006/0161017 A1 | 7/2006 | Grass et al. |
| 2006/0183936 A1 | 8/2006 | Grass et al. |
| 2006/0281959 A1 | 12/2006 | Krissmann et al. |
| 2007/0027346 A1 | 2/2007 | Kaizik et al. |
| 2007/0043245 A1 | 2/2007 | Kaizik et al. |
| 2007/0112219 A1 | 5/2007 | Ortmann et al. |
| 2007/0135665 A1 | 6/2007 | Wiese et al. |
| 2007/0149781 A1 | 6/2007 | Riermeier et al. |
| 2007/0197799 A1 | 8/2007 | Holz et al. |
| 2007/0282130 A1 | 12/2007 | Borgmann et al. |
| 2008/0021234 A1 | 1/2008 | Nierlich et al. |

FOREIGN PATENT DOCUMENTS

| | | |
|---|---|---|
| EP | 0 441 446 | 8/1991 |
| EP | 0 676 405 | 10/1995 |

OTHER PUBLICATIONS

U.S. Appl. No. 09/708,646, filed Nov. 9, 2000, Hess et al.
U.S. Appl. No. 10/505,879, filed Sep. 3, 2004, Borgmann.
U.S. Appl. No. 11/908,343, filed Sep. 11, 2007, Holz et al.
U.S. Appl. No. 12/065,091, filed Feb. 28, 2008, Hess et al.

*Primary Examiner*—Sikarl A Witherspoon
(74) *Attorney, Agent, or Firm*—Oblon, Spivak, McClelland, Maier & Neustadt, P.C.

(57) ABSTRACT

The invention relates to a process for reaction of a carbonylatable compound using a metal complex catalyst comprising a metal of transition group VIII and an organophosphorus ligand and in the presence of a stabilizer based on a sterically hindered secondary amine.

21 Claims, No Drawings

CARBONYLATION METHOD BY ADDING SECONDARY STERICALLY HINDERED AMINES

The invention relates to a carbonylation process for reaction of a carbonylatable compound in the presence of a metal complex catalyst comprising a metal of transition group VIII and an organophosphorus ligand and in the presence of a sterically hindered secondary amine.

Carbonylation processes are processes frequently employed in organic chemistry. Thus, aldehydes can be prepared from an olefin having one less carbon atom by catalytic hydroformylation (or oxo process). Hydrogenation of these aldehydes gives alcohols which are utilized, for example, for preparing plasticizers or as detergents. Oxidation of the aldehydes gives carboxylic acids which can be used, for example, for producing drying accelerators for surface coatings or as stabilizers for PVC.

The reaction between olefin compounds, carbon monoxide and hydrogen in the presence of a catalyst to give the aldehydes having one more carbon atom is known as hydroformylation (oxo process). As catalysts in these reactions, use is frequently made of compounds of the transition metals of groups 8 to 10 of the Periodic Table of the Elements, in particular compounds of rhodium and of cobalt. The hydroformylation using rhodium compounds generally offers the advantage of higher chemoselectivity and better raw materials utilization compared to catalysis using cobalt compounds and is thus usually more economical. The rhodium-catalyzed hydroformylation is usually carried out using complexes which comprise rhodium and preferably trivalent phosphorus compounds as ligands. Known ligands are, for example, compounds from the classes of the phosphines, phosphites and phosphonites. An overview of the hydroformylation of olefins may be found in B. CORNILS, W. A. HERRMANN, "Applied Homogeneous Catalysis with Organometallic Compounds", Vol. 1&2, VCH, Weinheim, New York, 1996.

Each catalyst system (cobalt or rhodium) has its specific advantages. Different catalyst systems are used depending on the starting material and target product. If rhodium and triphenylphosphine are employed, α-olefins can be hydroformylated at lower pressures and temperatures than when using cobalt catalysts. As phosphorus-containing ligand, it is usual to use an excess of triphenylphosphine, since a high ligand/rhodium ratio is necessary to increase the selectivity of the reaction to the commercially desired n-aldehyde product.

U.S. Pat. Nos. 4,694,109 and 4,879,416 relate to bisphosphine ligands and their use in the hydroformylation of olefins at low synthesis gas pressures. Particularly in the case of the hydroformylation of propene, high activities and high n/i selectivities are achieved using ligands of this type.

WO-A-95/30680 describes bidentate phosphine ligands and their use in catalysis, including use in hydroformylation reactions.

Ferrocene-bridged bisphosphines are disclosed as ligands for hydroformylations in, for example, U.S. Pat. Nos. 4,169,861, 4,201,714 and 4,193,943.

The disadvantage of bidentate phosphine ligands is the relatively complicated preparation. It is therefore often not cost-effective to use such systems in industrial processes. In addition, phosphite compounds are relatively unstable. Thus, EP 0 676 405 states that the storage stability of phosphites and phosphonites can be increased by addition of organic amines and an acid-binding metal salt.

Rhodium-monophosphite complexes are suitable catalysts for the hydroformylation of branched olefins having internal double bonds, but the selectivity to terminally hydroformylated compounds is low. EP-A-0 155 508 discloses the use of bisarylene-substituted monophosphites in the rhodium-catalyzed hydroformylation of sterically hindered olefins, e.g. isobutene.

Rhodium-bisphosphite complexes catalyze the hydroformylation of linear olefins having terminal and internal double bonds, forming predominantly terminally hydroformylated products, whereas branched olefins having internal double bonds in the vicinity of the branching point are frequently reacted to only a small extent. When coordinated to a transition metal center, these phosphites give catalysts having an increased activity, but the operating life of these catalyst systems is unsatisfactory because of, inter alia, the hydrolysis- and oxidation-sensitivity of the phosphite ligands. Significant improvements have been able to be achieved by use of substituted bisaryl diols as starting materials for the phosphite ligands, as described in EP-A-0 214 622 or EP-A-0 472 071.

According to the literature, the rhodium complexes of these ligands are extremely active hydroformylation catalysts for α-olefins. U.S. Pat. Nos. 4,668,651, 4,748,261 and 4,885,401 describe polyphosphite ligands by means of which α-olefins and also 2-butene can be converted with high selectivity into the terminally hydroformylated products. In U.S. Pat. No. 5,312,996, bidentate ligands of this type are also used for the hydroformylation of butadiene.

Although the organophosphorus compounds mentioned are good complexing ligands for rhodium hydroformylation catalysts, the complexing ligands or the catalyst system have/has a relatively high sensitivity which leads to the catalyst system or the ligands used being relatively quickly decomposed or oxidized under the conditions of most carbonylation reactions, including in the presence of industrially unavoidable traces of oxygen or peroxides.

In industrial processes, the complete exclusion of oxygen is difficult. In general, the starting olefins and the synthesis gas contain small amounts of oxygen and/or oxygen-containing compounds. Since the catalyst concentration is usually low in the carbonylation reactions carried out in industry because of the high price of the catalyst, even small amounts of oxygen introduced with the starting materials has a large adverse effect on the stability and activity of the ligands or metal complex catalysts. This can result in a decrease in the space-time yield, a reduction in the selectivity or an increased consumption of catalyst.

It is therefore an object of the invention to develop a carbonylation process which does not have one or more of the abovementioned disadvantages even when starting materials of customary industrial quality are used.

It has now surprisingly been found that the deactivation of the catalyst system by carbonylation reactions can be reduced by addition of sterically hindered secondary amines, i.e. secondary amines which have no hydrogen atom on the two carbon atoms bound directly to the nitrogen atom.

The present invention accordingly provides a carbonylation process in which at least one compound which is capable of being carbonylated by means of carbon monoxide is reacted with carbon monoxide in the presence of a metal complex catalyst of a metal of transition group VIII of the Periodic Table of the Elements which has an organophosphorus compound as ligand, wherein the carbonylation is carried out in the presence of a sterically hindered secondary amine having the general structural formula I

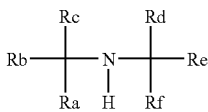

where Ra, Rb, Rc, Rd, Re and Rf are identical or different hydrocarbon radicals which may be joined to one another.

The present invention likewise provides a mixture comprising a metal complex catalyst of a metal of transition group VIII of the Periodic Table of the Elements which has an organophosphorus compound as ligand and a sterically hindered secondary amine having the general structural formula I

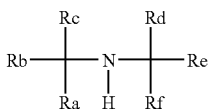

where Ra, Rb, Rc, Rd, Re and Rf are identical or different hydrocarbon radicals which may be joined to one another.

The process of the invention has the advantage that the stability of the catalyst system is significantly improved, particularly in respect of the oxidation sensitivity and/or hydrolysis sensitivity. Due to the improved oxidation sensitivity, it is possible to use starting materials which contain small amounts of oxygen as impurity. In addition, the reaction is simpler to carry out since 100% exclusion of oxygen is no longer absolutely necessary. Due to the improved thermal stability of the ligands, the carbonylation reactions can be carried out at relatively high temperatures at which rapid decomposition of the ligands is observed without the addition according to the invention of stabilizers. The ability to carry out the carbonylation reactions at higher temperatures makes it possible to increase the reaction rate.

The process of the invention is described by way of example below without the invention being restricted to these embodiments. A person skilled in the art will be able to devise further variants which are likewise subject matter of the present invention, whose scope is defined by the description and the claims.

In the carbonylation process of the invention, in which at least one compound which is capable of being carbonylated by means of carbon monoxide is reacted with carbon monoxide in the presence of a metal complex catalyst of a metal of transition group VIII of the Periodic Table of the Elements which has an organophosphorus compound, in particular a compound having at least one phosphorus-oxygen bond, as ligand, the carbonylation is carried out in the presence of a sterically hindered secondary amine having the general structural formula I,

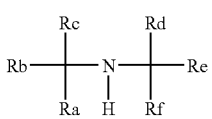

where Ra, Rb, Rc, Rd, Re and Rf are identical or different hydrocarbon radicals which may be joined to one another. The sterically hindered secondary amine of the formula I functions as stabilizer.

In the process of the invention, preference is given to using secondary amines which have a 2,2,6,6-tetramethylpiperidine unit II

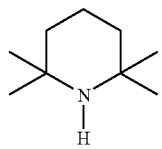

or 2,2,6,6-tetramethylpiperidine itself. Particular preference is given to using amines which have a 2,2,6,6-tetramethylpiperidine unit and are substituted in the 4 position and have the general structure IIa

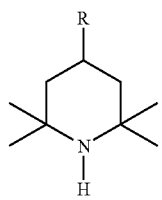

where R is an organic radical, a hydroxyl group or a halogen. The organic radical R can be, for example, an organic radical bound via a heteroatom, for example an oxygen atom, to the structural unit II'

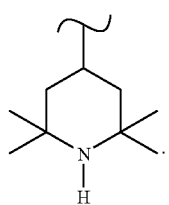

In particular, the organic radical can have a polymeric structure or be an organic radical having from 1 to 50 carbon atoms and, if desired, heteroatoms. The organic radical particularly preferably has carbonyl groups, e.g. keto, ester or acid amide groups. The organic, optionally heteroatom-containing radical can be, in particular, a substituted or unsubstituted, aliphatic, alicyclic, aliphatic-alicyclic, heterocyclic, aliphatic-heterocyclic, aromatic, aromatic-aromatic or aliphatic-aromatic hydrocarbon radical having from 1 to 50 carbon atoms, with substituted hydrocarbon radicals being able to bear substituents selected from among primary, secondary or tertiary alkyl groups, alicyclic groups, aromatic groups, —N($R^1$)$_2$, —NH$R^1$, —NH$_2$, fluorine, chlorine, bromine, iodine, —CN, —C(O)—$R^1$, —C(O)H or —C(O)O—$R^1$, —CF$_3$, —O—$R^1$, —C(O)N—$R^1$, —OC(O)—$R^1$ and/or —Si($R^1$)$_3$, where $R^1$ is a monovalent hydrocarbon radical which preferably has from 1 to 20 carbon atoms. If a plurality of hydrocarbon radicals $R^1$ are present, these can be identical or different. The substituents are preferably restricted to ones which have no influence on the reaction itself. Particularly preferred substituents can be selected from among halogens such as chlorine, bromine or iodine, alkyl radicals such as methyl, ethyl, propyl, isopropyl, butyl, sec-butyl, t-butyl, neopentyl, sec-amyl, t-amyl, isooctyl, t-octyl, 2-ethylhexyl, isononyl, isodecyl or octadecyl, aryl radicals such as phenyl, naphthyl or anthracyl, alkylaryl radicals such as tolyl, xylyl, dimethylphenyl, diethylphenyl, trimethylphenyl, triethylphenyl or p-alkylphenyl, aralkyl radicals such as benzyl or phenylethyl, alicyclic radicals such as cyclopentyl, cyclohexyl, cyclooctyl, cyclohexylethyl or 1-methylcyclohexyl, alkoxy radicals such as methoxy, ethoxy, propoxy, butoxy or pentoxy, aryloxy radicals such as phenoxy or naphthoxy, —OC(O)R$^1$ or —C(O)R$^1$, e.g. acetyl, propionyl, trimethylacetoxy, triethylacetoxy or triphenylacetoxy, and silyl radicals bearing three hydrocarbon radicals (—Si(R$^1$)$_3$), e.g. trimethylsilyl, triethylsilyl or triphenylsilyl. Particular preference is given to compounds of the formula IIa which bear radicals R which have, apart from the 2,2,6,6,-tetramethylpiperidine building block, not more than one, very particularly preferably no further —N(R$^1$)$_2$, —NHR$^1$ and/or —NH$_2$ group.

As secondary amines which have a structural unit of the formula II, very particular preference is given to using the compounds having the structural formulae IIb to IIg shown below or derivatives thereof.

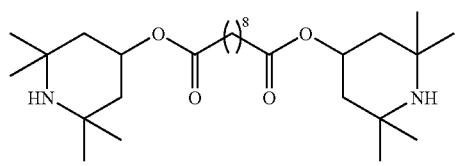

IIb

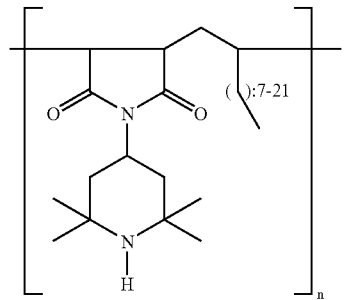

IIc where n=1 to 20, preferably from 1 to 10

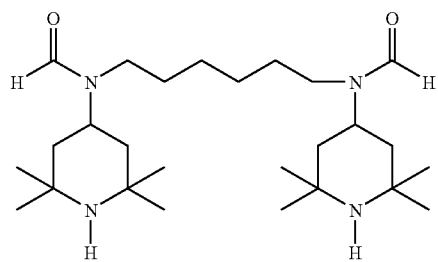

IId

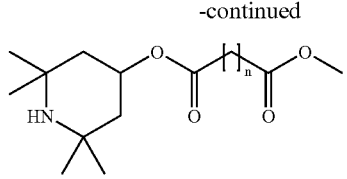

IIe where n=1 to 12, preferably 8

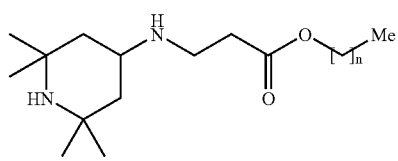

IIf where n=1 to 17, preferably 13

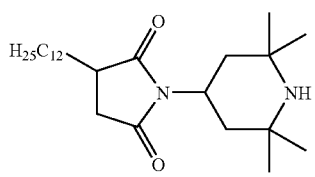

IIg

The compounds of the formula II are commonly known as HALS (hindered amine light stabilizers) and are used for stabilizing polymers against aging caused by light. Numerous publications (Pieter Gijsman, Polymer Degradation and Stability 43 (1994) 171-176; Peter P. Klemchuck, Matthew E. Gande, Polymer Degradation and Stability 22 (1988) 241-74; Peter P. Klemchuck, Matthew E. Gande, Makromol. Chem., Macromol. Symp. 28, 117-144, (1989)) are concerned with the mechanism of polymer stabilization, but no conclusive explanation has yet been given. Compounds of the formula II are commercially available and can be obtained, for example, from the companies ICI America, Sigma-Aldrich, Fluka, ABCR, Ciba, BASF and Degussa. The preparation of these compounds is, for example, outlined in Polymers & Polymer Composites, Vol. 8, No. 4, 2000.

The sterically hindered secondary amine I is preferably used in a molar ratio to the catalyst metal of from 0.1:1 to 100:1, more preferably in a ratio of from 2:1 to 50:1, in the reaction mixture. It can, for example, be introduced into the hydroformylation reactor together with the starting olefin and/or the recirculated catalyst solution. The amine is preferably introduced into the reaction together with the ligand. Preference is given to adding a compound of the formula II which is suitable as secondary amine as early as during the storage of the ligand or the complex used as catalyst.

It should be pointed out that, specifically in hydroformylation, it is possible to use the N-oxyls and N-hydroxy compounds derived from the hindered secondary amines instead of the hindered secondary amines themselves, since they are reduced to the sterically hindered secondary amines under the reaction conditions.

The carbonylation process of the invention is preferably carried out using trivalent compounds of the elements of main group V of the Periodic Table of the Elements (nitrogen, phosphorus, arsenic, antimony, bismuth) as ligands. In particular, trivalent organophosphorus ligands are used.

As organophosphorus ligands, it is possible to use, for example, the compounds shown below or compounds which contain at least one of the functional groups shown.

The compounds of the formula III $$PR^2R^3R^4 \qquad\qquad III$$

have exclusively organic radicals which are all bound via a carbon atom to the phosphorus atom as radicals $R^2$ to $R^4$, e.g. phosphines or a phosphino group.

The compounds of the formula IV $$PR^2R^3(TR^5) \qquad\qquad IV$$

have organic radicals which are all bound via a carbon atom to the phosphorus atom as radicals $R^2$ and $R^3$ and an organic radical which is bound via a heteroatom T selected from among oxygen and nitrogen to the phosphorus atom as radical $R^5$. In the case of T=oxygen, such compounds are, for example, phosphinites or a phosphinito group.

The compounds of the formula V $$PR^2(TR^5)(TR^6) \qquad\qquad V$$

have an organic radical which is bound via a carbon atom to the phosphorus atom as radical $R^2$ and an organic radical which is bound via a heteroatom T selected from among oxygen and nitrogen to the phosphorus atom as radical $R^5$ and $R^6$, with the heteroatoms being able to be identical or different. When T is in each case oxygen, such compounds are, for example, phosphonites or a phosphinito group.

The compounds of the formula VI $$P(TR^5)(TR^6)(TR^7) \qquad\qquad VI$$

have an organic radical which is bound via a heteroatom T selected from among oxygen and nitrogen to the phosphorus atom as radicals $R^5$ to $R^7$, with the heteroatoms being able to be identical or different. When T is in each case oxygen, such compounds are, for example, phosphites or a phosphito group.

In the structural formulae III to VI, T is oxygen, NH or $NR^8$. The radicals $R^2$ to $R^8$ are identical or different organic radicals which have from 1 to 50 carbon atoms and may be joined to one another.

As mentioned above, it is also possible to use, in particular, compounds having two or more functional groups of the groups III to VI as ligands in the process of the invention.

If a compound having two functional organophosphorus groups is present, one of the radicals $R^2$ to $R^7$ is divalent (cf., for example, formula VIIb, in which the radical $R^2$ is divalent). It connects the two functional groups and can be assigned to either. In the case of compounds having three functional phosphorus groups, one of the radicals $R^2$ to $R^7$ is trivalent or two of the radicals $R^2$ to $R^7$ are divalent. The polyvalent radicals connect the functional groups to one another. An analogous situation applies to compounds having more than three organophosphorus groups.

General classes of compounds for such bifunctional organophosphorus compounds are, for example, bisphosphines (combination of III with III), bisphosphinites (combination of IV with IV, when T is in each case an oxygen atom), bisphosphonites (combination of V with V, when all radicals T are oxygen atoms) or bisphosphites (combination of VI with VI, when all radicals T are oxygen atoms). In addition, each functional group (III to VI) can be combined with another functional group (III to VI), for example phosphinite-phosphites (IV combined with V, when all radicals T are oxygen atoms). An analogous situation applies to compounds of at least three different types (III to VI) of organophosphorus groups.

The carbonylation process of the invention is preferably carried out using a compound of the Formula $$R^2[PR^3R^4]_x, \qquad\qquad VII$$

where x=an integer from 1 to 10, preferably from 1 to 4 and particularly preferably 2, $R^2$=an x-valent organic radical and $R^3$ and $R^4$=an organic radical, with $R^3$ and $R^4$ being able to be identical or different and being able to be bound covalently to one another and when x is $\geqq 2$, the radicals $R^3$ and $R^4$ of the $[PR^3R^4]$ structural units being able to be identical or different, as organophosphorus ligand. In the process of the invention, particular preference is given to using at least one compound selected from among the formulae VIIa, VIIb and VIIc $$R^2[PR^3R^4] \qquad\qquad VIIa$$

$$[R^3R^{4'}P]R^2[PR^3R^4] \qquad\qquad VIIb$$

$$[R^3R^{4'}P]R^2[PR^{3'}R^{4'}] \qquad\qquad VIIc$$

where $R^3$, $R^4$, $R^{3'}$ and $R^{4'}$=an organic radical, with $R^3$ and $R^{3'}$ and/or $R^4$ and $R^{4'}$ being different and the radicals $R^3$ and $R^4$ and also $R^{3'}$ and $R^{4'}$ being able to be identical or different and being able to be covalently bound to one another, as organophosphorus ligand. The compounds of the formula VIIb are a special case of the compounds of the formula VIIc in which the organophosphorus radicals —$[PR^3R^4]$ are identical. The radicals $R^2$, $R^3$, $R^4$, $R^{3'}$ and $R^{4'}$ are preferably organic radicals which have no heteroatom or can have, for example, oxygen or sulfur as heteroatoms. The radicals $R^2$, $R^3$, $R^4$, $R^{3'}$ and $R^{4'}$ are particularly preferably organic radicals which are bound via a heteroatom, preferably oxygen or nitrogen, to the phosphorus or organic radicals, in particular hydrocarbon radicals, which are bound via a carbon atom to the phosphorus.

Possible compounds of ligands of the formula VII are phosphines, phosphinites, phosphonites or phosphites, or when two or more organophosphorus groups are present, bisphosphites or polyphosphites, bisphosphinites or polyphosphinites or bisphosphonites or polyphosphonites or else ligands which have two or more different organophosphorus groups, e.g. phosphonite-phosphonites, phosphinite-phosphites or phosphonite-phosphites. The radicals $R^2$, $R^3$, $R^4$, $R^{3'}$ and $R^{4'}$ are accordingly preferably organic radicals which are bound directly or via an oxygen atom to the phosphorus, in particular hydrocarbon radicals which may be substituted or unsubstituted. The ligands of the formula VII are preferably not phosphoramidite compounds.

Among phosphine ligands, substituted trialkylphosphine or triarylphosphine compounds are particularly suitable for use in the process of the invention. Preferred phosphine ligands are, for example, substituted or unsubstituted triphenylphosphines, in particular triphenyl-phosphines in which at least one of the phenyl radicals bears a sulfonate radical. Particularly preferred phosphines are selected from among: triphenylphosphine, tris(p-tolyl)phosphine, tris(m-tolyl)phosphine, tris(o-tolyl)phosphine, tris(p-methoxyphenyl)phosphine, tris(p-dimethylaminophenyl)phosphine, tricyclohexylphosphine, tricyclopentylphosphine, triethylphosphine, tri(1-naphthyl)phosphine, tribenzylphosphine, tri-n-butylphosphine, tri-t-butylphosphine.

Customary phosphonite ligands are described, inter alia, in U.S. Pat. No. 5,710,344, WO-A-95/06627, U.S. Pat. No. 5,360,938 or JP-A-07-082281. Examples are diphenyl(phenoxy)phosphine and its derivatives in which all or some of the hydrogen atoms are replaced by alkyl and/or aryl radicals or halogen atoms, diphenyl(methoxy)phosphine and diphenyl (ethoxy)phosphine.

As phosphonite ligands, it is possible to use all ligands which have at least two organic radicals bound via an oxygen atom and one organic radical bound via a carbon atom, with two or more of these radicals being able to be covalently bound to one another. Examples of phosphonites which can be used in the process of the invention are methyldiethoxyphosphine, phenyldimethoxyphosphine, phenyldiphenoxyphosphine, 2-phenoxy-2H-dibenz[c,e][1,2]oxa-phosphorin and its derivatives in which all or some of the hydrogen atoms are replaced by alkyl and/or aryl radicals or halogen atoms and ligands which are described in WO-A-98/43935, JP-A-09-268152 and DE-A-198 10 794 and in the German patent applications DE-A-199 54 721 and DE-A-199 54 510. Ligands which are particularly suitable for the process of the invention and in particular for a hydroformylation are described, for example, by the general formulae disclosed in DE-A-199 54 721. Phosphonite ligands which are very particularly preferably used in the process of the invention are ones selected from among the compounds of the formulae VIIa-1 to VIIa-24:

VIIa-1

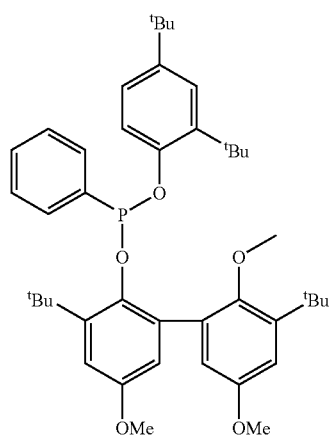

VIIa-2

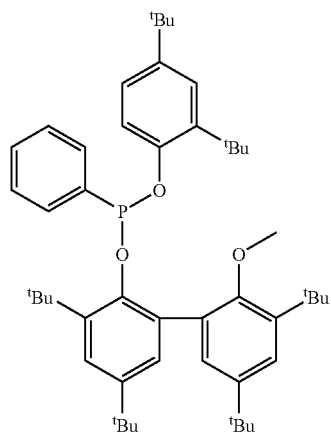

-continued

VIIa-3

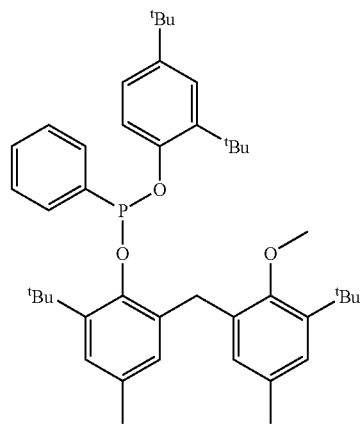

VIIa-4

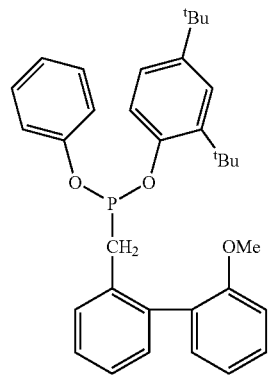

VIIa-5

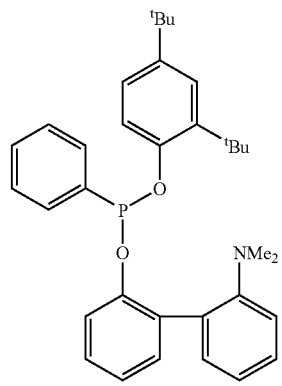

VIIa-6

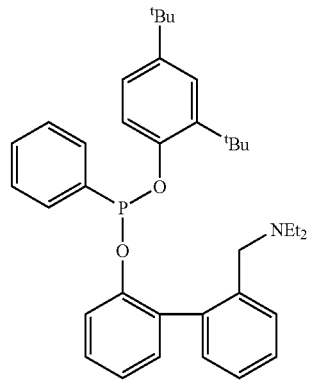

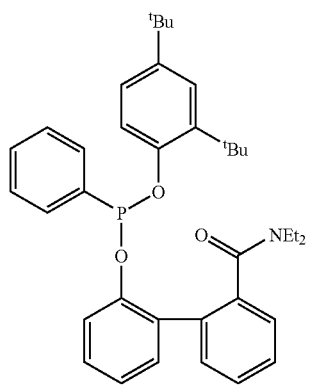
VIIa-7
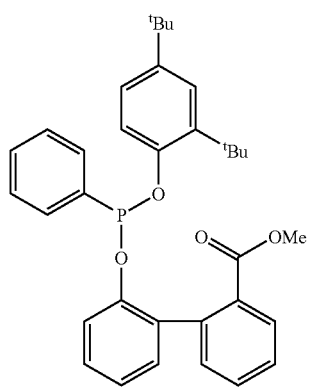
VIIa-8
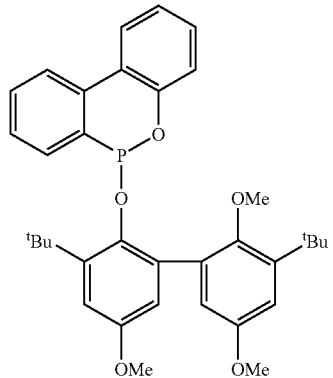
VIIa-9
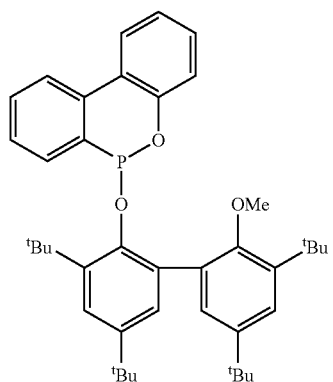
VIIa-10
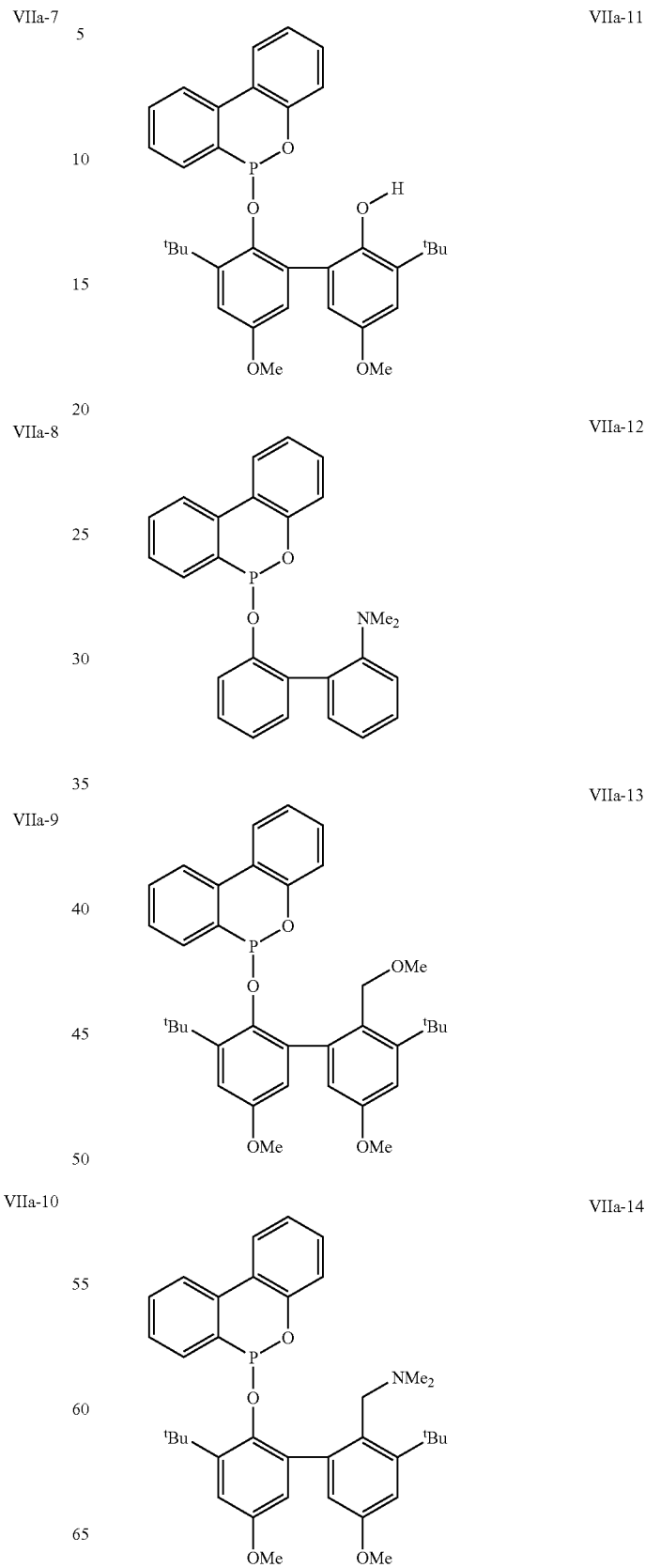

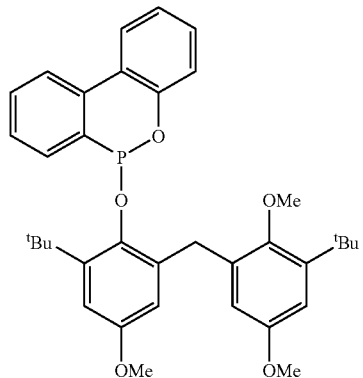 VIIa-15
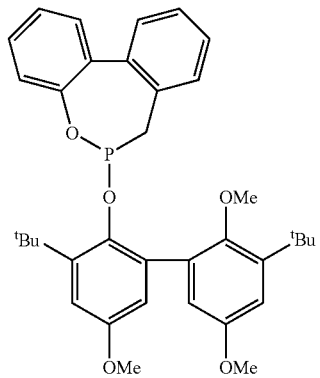 VIIa-19
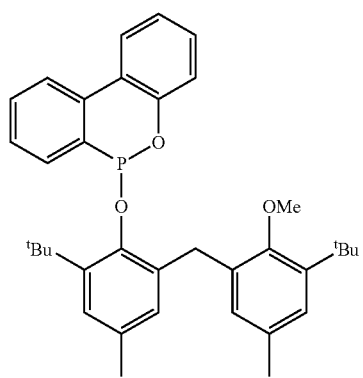 VIIa-16
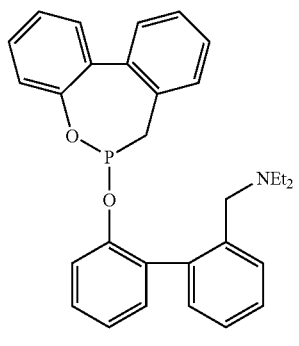 VIIa-20
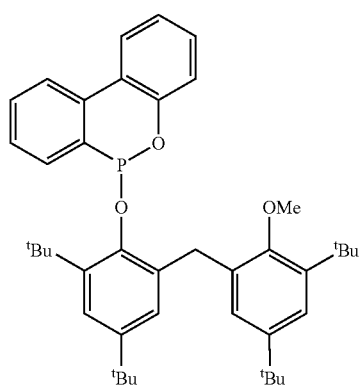 VIIa-17
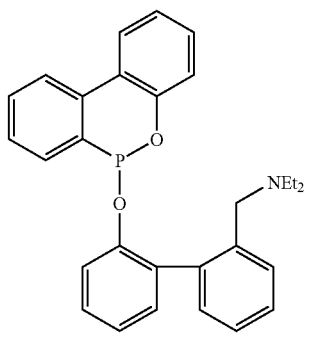 VIIa-21
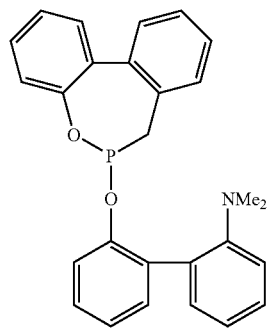 VIIa-18
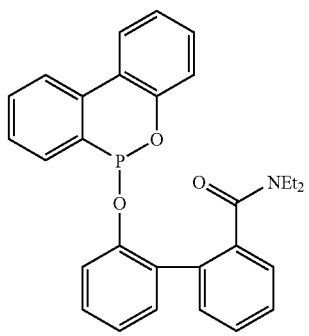 VIIa-22

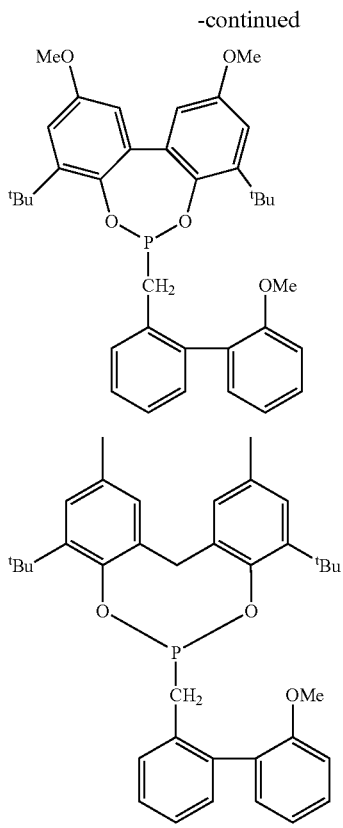

VIIa-23

VIIa-24

Phosphites are well-suited ligands for the process of the invention. Substituted trialkyl phosphite or triaryl phosphite compounds are particularly suitable for use as phosphite ligands in the process of the invention. Particularly preferred phosphite ligands are, for example, substituted or unsubstituted triphenyl phosphites, in particular triphenyl phosphites in which at least one of the phenyl radicals bears a sulfonate radical. Examples of phosphites are: trimethyl phosphite, triethyl phosphite, tri-n-propyl phosphite, tri-i-propyl phosphite, tri-n-butyl phosphite, tri-i-butyl phosphite, tri-t-butyl phosphite, tris(2-ethylhexyl) phosphite, triphenyl phosphite, tris(2,4-di-t-butylphenyl) phosphite, tris(2-t-butyl-4-methoxyphenyl) phosphite, tris(2-t-butyl-4-methylphenyl) phosphite, tris(p-cresyl) phosphite. In addition, sterically hindered phosphite ligands as are described, inter alia, in EP-A-155 508, U.S. Pat. Nos. 4,668,651, 4,748,261, 4,769,498, 4,774,361, 4,835,299, 4,885,401, 5,059,710, 5,113,022, 5,179,055, 5,260,491, 5,264,616, 5,288,918, 5,360,938, EP-A-472 071, EP-A-518 241 and WO-A-97/20795 are suitable ligands.

Possible ligands of the formula VIIc are phosphite-phosphine compounds, phosphite-phosphonite compounds, phosphite-phosphinite compounds, phosphite-phosphite compounds, phosphine-phosphine compounds, phosphinite-phosphine compounds, phosphonite-phosphine compounds, phosphonite-phosphinite compounds, phosphinite-phosphinite compounds or phosphonite-phosphonite compounds. Possible compounds of ligands of the formula VIIb are bisphosphines, bisphosphinites, bisphosphonites and bisphosphites.

Bisphosphines which can be used for the process of the invention and their preparation are described, for example, in WO 02/076996. The bisphosphines described there which are preferred for the process of the invention are ones in which $R^2$ is a divalent substituted or unsubstituted alkylaryl radical (—$CH_2$—Ar—$CH_2$—) [$R^4R^3P$]—$R^2$—[$PR^{3'}R^{4'}$]. Diphosphines of the formula [$R^4R^3P$]—Ar—[$PR^{3'}R^{4'}$] in which the radical $R^2$ is a divalent aryl radical Ar are likewise suitable for the process of the invention.

Compounds of the formula VIIc can, for example, be the following compounds.

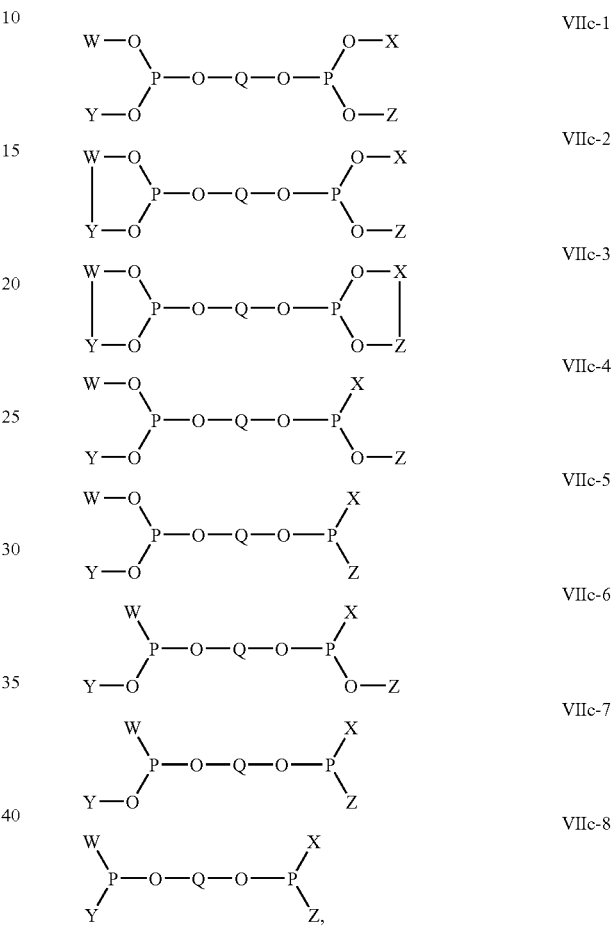

where W, X, Y and Z are substituted or unsubstituted, aliphatic, alicyclic, aliphatic-alicyclic, heterocyclic, aliphatic-heterocyclic, aromatic-aromatic or aliphatic-aromatic hydrocarbon radicals having from 1 to 50 carbon atoms, with W, X, Y and Z being able to be identical or different or be covalently bound to one another, and Q is an at least divalent, substituted or unsubstituted aliphatic, alicyclic, aliphatic-alicyclic, heterocyclic, aliphatic-heterocyclic, aromatic, aromatic-aromatic or aliphatic-aromatic hydrocarbon radical having from 1 to 50 carbon atoms. The substituted hydrocarbon radicals may have one or more substituents selected from among primary, secondary or tertiary alkyl groups, alicyclic groups, aromatic groups, —$N(R^8)_2$, —$NHR^9$, —$NH_2$, fluorine, chlorine, bromine, iodine, —CN, —C(O)—$R^{10}$, —C(O)H or —C(O)O—$R^{11}$, —$CF_3$, —O—$R^{12}$, —C(O)N—$R^{13}$, —OC(O)—$R^{14}$ and/or —$Si(R^{15})_3$, where $R^8$ to $R^{15}$ are each a monovalent hydrocarbon radical which preferably has from 1 to 20 carbon atoms. If a plurality of hydrocarbon radicals $R^8$ to $R^{15}$ are present, these can be identical or different. The substituents are preferably restricted to ones which have no influence on the reaction itself. Particularly preferred substituents can be selected from among halogens such as chlorine, bromine or iodine, alkyl radicals such as methyl, ethyl, propyl, isopropyl, butyl, sec-butyl, t-butyl, neopentyl, sec-amyl, t-amyl, isooctyl, t-octyl, 2-ethylhexyl, isononyl, isodecyl or octadecyl, aryl radicals such as phenyl, naphthyl or anthracyl, alkylaryl radicals such as tolyl, xylyl, dimethylphenyl, diethylphenyl, trimethylphenyl, triethylphenyl or p-alkylphenyl, aralkyl radicals such as benzyl or phenylethyl, alicyclic radicals such as cyclopentyl, cyclohexyl, cyclooctyl, cyclohexylethyl or 1-methylcyclohexyl, alkoxy radicals such as methoxy, ethoxy, propoxy, butoxy or pentoxy, aryloxy radicals such as phenoxy or naphthoxy, —OC(O)$R^{14}$ or —C(O)$R^{10}$, e.g. acetyl, propionyl, trimethylacetoxy, triethylacetoxy or triphenylacetoxy, and silyl radicals bearing three hydrocarbon radicals (—Si(hydrocarbyl)$_3$), e.g. trimethylsilyl, triethylsilyl or triphenylsilyl.

Examples of compounds which can be used as bisphosphites in the process of the invention are described, for example, in WO 02/00670, with the "Formula III" mentioned there (not identical to the formula III of this patent text) being compounds which correspond to the formula VIIb of the present invention. The description of WO 02/00670 is incorporated by reference into the present disclosure.

A particular form of the bisphosphites encompasses the bisacyl phosphites or acyl phosphite-phosphites in which the structural unit S

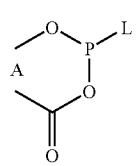

(S)

where A is a divalent substituted or unsubstituted alkyl or aryl radical which can form a ring system corresponding to the structural unit S and the radical L is an organic radical bound via an oxygen or carbon atom to the phosphorus atom, is present twice or once. A specific embodiment of bisacyl phosphites is disclosed, for example, in WO 03/016320 as the formulae I and II (in each case with k=2). The compounds of the formulae A to H disclosed in WO 03/016320 correspond to the formula VIIb of the present invention, while the compounds of the formulae I to M in WO 03/016320 are examples of compounds of the formula VIIc which can also be used as organophosphorus ligand in the process of the invention. The description of WO 03/016320 is incorporated by reference into the present disclosure.

General examples of acyl phosphite compounds of the formula VIIc are the following compounds:

VIIc-9

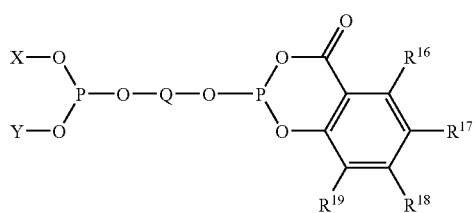

VIIc-10

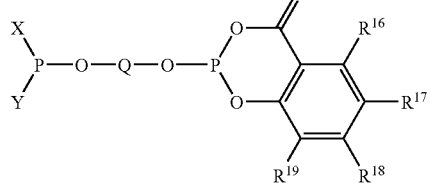

VIIc-11

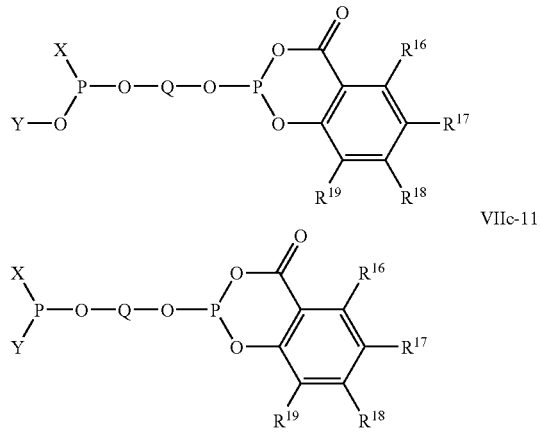

where X and Y are substituted or unsubstituted, aliphatic, alicyclic, aliphatic-alicyclic, heterocyclic, aliphatic-heterocyclic, aromatic-aromatic or aliphatic-aromatic hydrocarbon radicals having from 1 to 50 carbon atoms, with X and Y being identical or different or being covalently bound to one another, and Q is an at least divalent, substituted or unsubstituted aliphatic, alicyclic, aliphatic-alicyclic, heterocyclic, aliphatic-heterocyclic, aromatic, aromatic-aromatic or aliphatic-aromatic hydrocarbon radical preferably having from 1 to 50 carbon atoms, with substituted hydrocarbon radicals having substituents selected from among —N($R^{20}$)$_2$, —NH$R^{20}$, —NH$_2$, fluorine, chlorine, bromine, iodine, —OH, —CN, —C(O)—$R^{20}$, —C(O)H or —C(O)O—$R^{20}$, —CF$_3$, —O—$R^{20}$, —C(O)N—$R^{20}$, —OC(O)—$R^{20}$ and/or —Si($R^{20}$)$_3$, where $R^{20}$ is a monovalent hydrocarbon radical which preferably has from 1 to 20 carbon atoms and if a plurality of hydrocarbon radicals $R^{20}$ are present, these can be identical or different, and $R^{16}$ to $R^{19}$ are selected independently from among monovalent substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having 1 to 50 carbon atoms, H, F, Cl, Br, I, —CF$_3$, —CH$_2$(CF$_2$)$_j$CF$_3$ where j=0-9, —O$R^{21}$, —CO$R^{21}$, —CO$_2$$R^{21}$, —CO$_2$M, —S$R^{21}$, —SO$_2$$R^{21}$, —SO$R^{21}$, —SO$_3$$R^{21}$, —SO$_3$M, —SO$_2$N$R^{21}$$R^{22}$, —N$R^{21}$$R^{22}$, —N=C$R^{21}$$R^{22}$ where $R^{21}$ and $R^{22}$ are selected independently from among H, monovalent substituted or unsubstituted aliphatic and aromatic hydrocarbon radicals having from 1 to 25 carbon atoms and M is an alkali metal ion, formally half an alkaline earth metal, ammonium or phosphonium ion, or adjacent radicals $R^{16}$ to $R^{19}$ together form a fused substituted or unsubstituted aromatic, heteroaromatic, aliphatic, mixed aromatic-aliphatic or mixed heteroaromatic-aliphatic ring system; with substituted hydrocarbon radicals having substituents selected from among —N($R^{23}$)$_2$, —NH$R^{23}$, —NH$_2$, fluorine, chlorine, bromine, iodine, —OH, —CN, —C(O)—$R^{23}$, —C(O)H or —C(O)O—$R^{23}$, —CF$_3$, —O—$R^{23}$, —C(O)N—$R^{23}$, —OC(O)—$R^{23}$ and/or —Si($R^{23}$)$_3$, where $R^{18}$ is a monovalent hydrocarbon radical which preferably has from 1 to 20 carbon atoms and when a plurality of hydrocarbon radicals $R^{23}$ are present, these can be identical or different, and the radicals $R^{16}$, $R^{17}$, $R^{18}$ and $R^{19}$ are identical or different.

A general formula for bisacyl phosphite compounds which are preferably used as ligands in the process of the invention is given by the formulae VIIb-1 and VIIb-2.

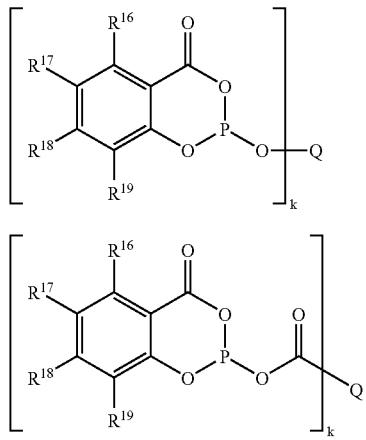

VIIb-1

VIIb-2 where k=2 and $R^{16}$, $R^{17}$, $R^{18}$, and $R^{19}$ having the meanings given for the formulae VIIc-9 to VIIc-11, Q is a divalent substituted or unsubstituted aliphatic, alicyclic, mixed aliphatic-alicyclic, heterocyclic, mixed aliphatic-heterocyclic, aromatic, heteroaromatic, mixed aliphatic-aromatic hydrocarbon radical having from 1 to 50 carbon atoms, with aliphatic parts of Q being able to contain oxygen, sulfur and/or nitrogen and substituted hydrocarbon radicals Q being able to have substituents having the same meanings as $R^{16}$ to $R^{19}$. The preparation of such compounds and also further preferred embodiments may be found in WO 03/016320, whose description is incorporated by reference into the present disclosure.

As starting compound to be carbonylated, it is possible to use, for example, an olefinically unsaturated compound selected from among alpha-olefins, internal olefins, cycloolefins, alkenyl alkyl ethers and alkenols, with these compounds each being able to be substituted or unsubstituted, in the process of the invention. Examples of suitable alpha-olefinic compounds are propene, butene, pentene, butadiene, pentadiene, 1-hexene, 1-heptene, 1-octene, 1-nonene, 1-decene, 1-undecene, 1-dodecene, 1-hexadecene, 2-ethyl-1-hexene, 1,4-hexadiene, 1,7-octadiene, 3-cyclohexyl-1-butene, styrene, 4-vinylcyclohexene, allyl acetate, vinyl formate, vinyl acetate, vinyl propionate, allyl methyl ether, vinyl methyl ether, vinyl ethyl ether, allyl alcohol, 3-phenyl-1-propene, hex-1-en-4-ol, oct-1-en-4-ol, 3-butenyl acetate, allyl propionate, allyl butyrate, n-propyl-7-octenoate, 7-octenoic acid, 5-hexenamide, 1-methoxy-2,7-octadiene and 3-methoxy-1,7-octadiene. If the process of the invention is a hydroformylation, the starting compounds to be carbonylated are preferably selected from among olefins and mixtures of olefins. In particular, it is possible to use monoolefins having from 3 to 24, preferably from 4 to 16, particularly preferably from 3 to 12, carbon atoms and terminal or internal C—C double bonds, e.g. 1- or 2-pentene, 2-methyl-1-butene, 2-methyl-2-butene, 3-methyl-1-butene, 1-, 2- or 3-hexene, the $C_6$-olefin mixture formed in the dimerization of propene (dipropene), heptenes, 2- or 3-methyl-1-hexene, octenes, 2-methylheptenes, 3-methylheptenes, 5-methyl-2-heptene, 6-methyl-2-heptene, 2-ethyl-1-hexene, the isomeric $C_8$-olefin mixture formed in the dimerization of butenes (dibutene), nonenes, 2- or 3-methyloctenes, the $C_9$-olefin mixture formed in the trimerization of propene (tripropene), decenes, 2-ethyl-1-octene, dodecenes, the $C_{12}$-olefin mixture formed in the tetramerization of propene or the trimerization of butenes (tetrapropene or tributene), tetradecenes, hexadecenes, the $C_{16}$-olefin mixture formed in the tetramerization of butenes (tetrabutene) and olefin mixtures prepared by cooligomerization of olefins having different numbers of carbon atoms (preferably from 2 to 4), if appropriate after fractional distillation to give fractions having an identical or similar chain length. It is likewise possible to use olefins or olefin mixtures which have been produced by Fischer-Tropsch synthesis and also olefins which have been obtained by oligomerization of ethene or olefins which can be obtained via metathesis reactions. Preferred starting materials are $C_4$-, $C_8$-, $C_9$-, $C_{12}$- or $C_{16}$-olefin mixtures.

In addition to the carbon monoxide and the starting compound to be carbonylated, at least one compound selected from among hydrogen, water, amine and alcohol can be used as further reactant in the process of the invention. Particular preference is given to using at least hydrogen as further reactant in addition to carbon monoxide and the starting compound to be carbonylated. For example, this is used in the form of synthesis gas and a hydroformylation reaction is carried out.

The process of the invention can be carried out using various catalysts and/or ligands.

Possible catalytically active metals are the metals of transition group VIII of the Periodic Table of the Elements, e.g. rhodium, cobalt, platinum or ruthenium, with particular preference being given to using cobalt or rhodium as metal of transition group VIII of the Periodic Table of the Elements.

The active catalyst complex for the carbonylation is formed from a salt or a compound of the metal (catalyst precursor), the ligand, the carbon monoxide and, if applicable, the further reactant, in the case of hydroformylation of the hydrogen. This advantageously occurs in situ during the carbonylation reaction (i.e., for example, during the hydroformylation). Customary catalyst precursors are, for example, octanoates or acetylacetonates.

If the process of the invention is a hydroformylation, this is preferably carried out according to known methods, as described, for example, in J. FALBE, "New Syntheses with Carbon Monoxide", Springer Verlag, Berlin, Heidelberg, New York, page 95 ff., (1980).

The molar ratio of metal to ligand is preferably from 0.1/1 to 1/1000, more preferably from 1/1 to 1/100 and particularly preferably from 1/1 to 1/50. The carbonylation process of the invention is preferably carried out using the organophosphorus ligand in such a molar ratio to the metal that the ligand is also present as free ligand in the reaction mixture. The concentration of the metal in the reaction mixture is in the range from 1 ppm by mass to 1000 ppm by mass, preferably in the range from 5 ppm by mass to 300 ppm by mass.

Fresh ligand can be added to the reaction at any point in time in order to keep the concentration of free ligand constant. The transition metal complex catalysts can be synthesized before use. However, the catalytically active complexes are generally formed in situ in the reaction medium from a catalyst precursor and the organophosphorus ligands.

In the case of a hydroformylation, the reaction temperature in the process of the invention is preferably from 60° C. to 180° C., more preferably from 90° C. to 150° C., and the pressures are preferably from 1 to 300 bar, more preferably from 15 to 60 bar. The molar ratio of hydrogen to carbon monoxide ($H_2$/CO) in the synthesis gas used in the hydroformylation is preferably from 10/1 to 1/10 and more preferably from 1/2 to 2/1.

The catalyst, i.e. the metal and ligand, is preferably homogeneously dissolved in the carbonylation mixture comprising starting material (olefin) and products (aldehydes, alcohols, high boilers). A solvent, e.g. toluene, Texanol, Diphyl (eutectic mixture of biphenyl and diphenyl ether), high-boiling residues, phthalates such as di(2-ethylhexyl) phthalate or dinonyl phthalates, or esters of 1,2-cyclohexanoic acids, can optionally be used in addition.

If the carbonylation reaction according to the invention is a hydroformylation, this can be carried out continuously or batchwise. Examples of industrial apparatuses in which the reaction can be carried out are stirred vessels, bubble columns, jet nozzle reactors, tube reactors and loop reactors, some of which can be cascaded and/or provided with internals.

The reaction can be carried out in one or more stages. The separation of the aldehyde compounds formed and the catalyst can be carried out by a conventional method, e.g. fractionation. In industry, this can be effected, for example, by a distillation, by means of a falling film evaporator or a thin film evaporator. This is particularly useful when the catalyst dissolved in a high-boiling solvent is separated from the lower-boiling products. The catalyst solution which has been separated off, in which the predominant part of the secondary amine of the formula I which is used is preferably also present, can be used for a further hydroformylation. When lower olefins (e.g. propene, butene, pentene) are used, discharge of the products from the reactor via the gas phase is also possible.

Carbonylation reactions, in particular hydroformylation reactions, can be carried out by means of the process of the invention with only a small loss of ligand or catalyst system occurring. Apart from the therefore lower costs incurred for replacement of the ligand or the catalyst system itself, smaller amounts of by-products which result from decomposition of the ligand and would otherwise have to be removed are obtained in the process of the invention.

When carrying out the process of the invention, mixtures comprising a metal complex catalyst of a metal of transition group VIII of the Periodic Table of the Elements which has an organophosphorus compound as ligand and a sterically hindered secondary amine having the general structural formula I,

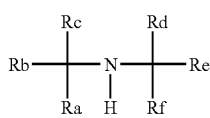

I where Ra, Rb, Rc, Rd, Re and Rf are identical or different hydrocarbon radicals which may be joined to one another, are obtained or used. A mixture according to the invention preferably comprises an amine having a 2,2,6,6-tetramethylpiperidine unit II

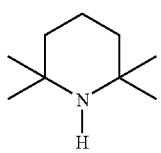

II as secondary amine.

In particular, the mixture can comprise the abovementioned secondary amines, in particular ones of the formula IIa. The mixture of the invention particularly preferably comprises at least one compound selected from among the compounds of the formulae IIb to IIg or derivatives thereof:

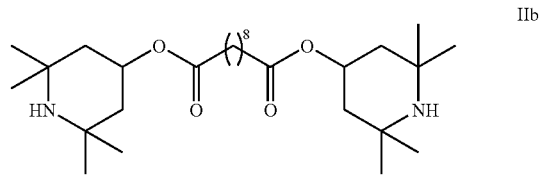

IIb

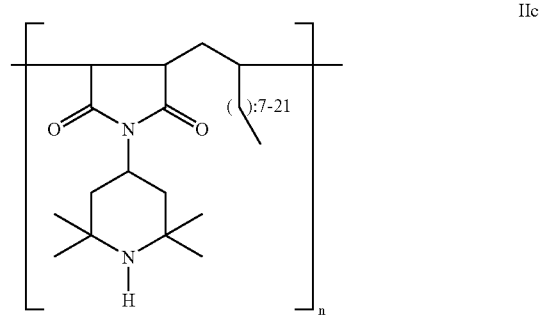

IIc where n=1 to 20, preferably from 1 to 10

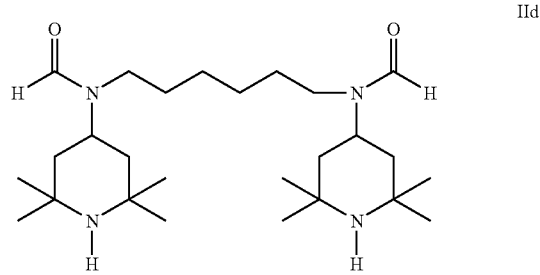

IId

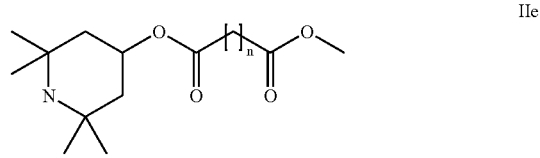

IIe where n=1 to 10, preferably 8

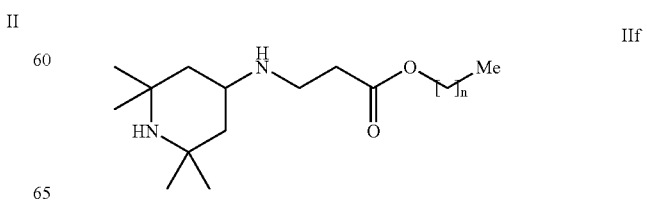

IIf where n=1 to 17, preferably 13

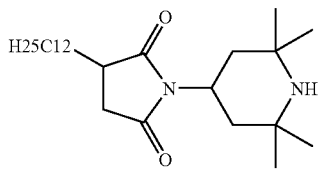

as secondary amine.

The mixtures of the invention preferably comprise at least one compound of the formula III to VI or a compound containing at least two functional groups of the formula III to VI as organophosphorus ligand. The mixtures of the invention more preferably comprise a compound of the formula VIIa, VIIb or VIIc as organophosphorus ligand. The mixtures of the invention particularly preferably comprise at least one compound of the formula VIIc-9, VIIc-10 or VIIc-11, very particularly preferably at least one compound of the formula VIIIb-1 or VIIb-2 as organophosphorus ligands.

In the mixture of the invention, the organophosphorus ligand is preferably present in a molar ratio to the metal of from 0.1:1 to 100:1, more preferably from 1:1 to 50:1. The mixture can comprise the abovementioned metals as metal of transition group VIII of the Periodic Table. However, the mixture preferably comprises cobalt or rhodium as metal of transition group VIII of the Periodic Table of the Elements.

The secondary amine compound of the formula I is preferably present in the mixture of the invention in a molar ratio to the catalyst metal of from 0.1:1 to 100:1, more preferably in a molar ratio of from 2:1 to 50:1.

The mixture of the invention can consist exclusively of the metal complex catalyst, if desired free organophosphorus ligand and the secondary amine of the formula I. The mixture of the invention preferably comprises not only these components but also further components, e.g. at least one solvent, starting materials, products, catalyst precursors or products formed from the catalyst or the catalyst precursor. The solvent can be any substance which is inert in the reaction in which the mixture of the invention is used. If the mixture of the invention is to be used as catalyst solution in a carbonylation process, in particular a hydroformylation process, it can be advantageous to use a product of the carbonylation reaction, e.g. the aldehyde product, as solvent. This makes it possible to avoid unnecessary contamination of the reaction product. However, the mixtures of the invention also include reaction mixtures obtained when using the above-described catalyst complexes and stabilizers.

The following examples illustrate the invention but do not restrict its scope which is defined by the description and the claims.

EXAMPLES

Example 1

Preparation of the Ligand Used

In this example, the preparation of the ligand IX used in example 2 will firstly be described.

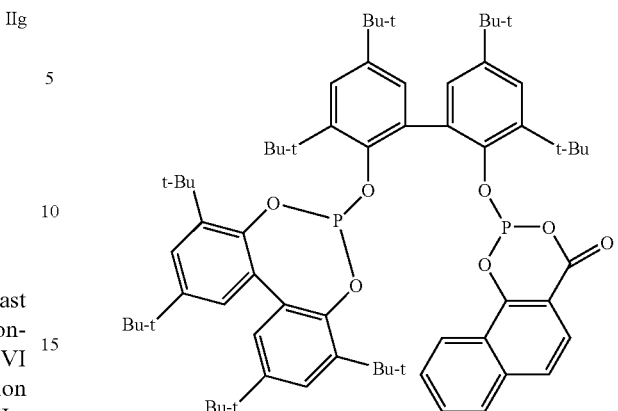

Ligand IX (of the Type VIIc)

Further information on the preparation of the intermediates and ligands described below may be found in, for example, J. Mol. Cat., 1983, 83, 17 and U.S. Pat. No. 4,885,401. The preparation of analogous ligands is described, for example, in EP 1 201 675. The preparation of chloro-naphthyldioxaphosphorinone analogs is, for example, also described in BE 667036.

Example 1.1

Preparation of 2,2'-bis(3,5-di-tert-butyl)phenol (L002)

Reaction equation:

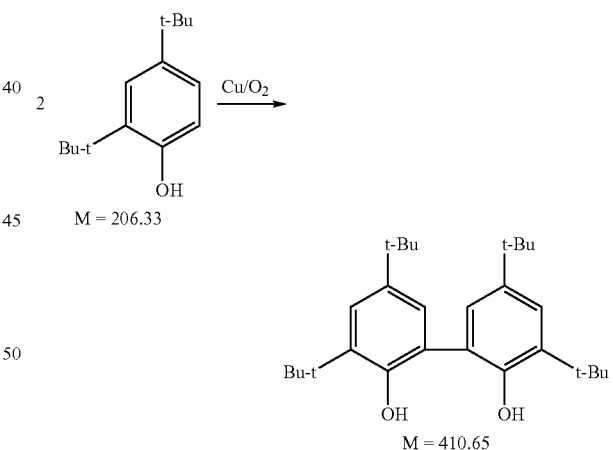

2 l of methanol were placed in a 4 l reaction flask provided with precision glass stirrer (Teflon blade stirrer), internal temperature sensor, inlet tube with frit (for air), reflux condenser and outlet with "bubbler" in the offgas line. 1000 g (4.85 mol) of 2,4-di-tert-butylphenol were then dissolved therein with vigorous stirring. 4 g (23.5 mmol) of copper chloride dihydrate and 4 ml (26.5 mmol) of N,N,N',N'-tetramethylethylenediamine were subsequently added to the stirred solution. The reaction solution was then stirred at room temperature while passing in air, recognizable by vigorous "bubbling". Small losses of solvent were compensated by making up with methanol. To make up for losses due to evaporation caused by "stripping", another 4 ml of N,N,N',N'-tetramethylethylenediamine were added after a prolonged reaction time. During the duration of the experiment, the product precipitated from the greenish blue reaction solution as a light-colored sediment.

For the work-up, the precipitated salt is filtered off with suction. It is then washed 3 times with 100 ml of methanol which has been cooled to 0° C. The salt was subsequently distributed over a large area on a metal dish and dried at 55° C. in a vacuum drying oven for 24 hours. The yield was about 70%. The purity was >99% by mass.

Example 1.2

Preparation of chlorophosphite (L008_01) from 2,2'-bis(3,5-di-tert-butyl)phenol (L002)

Reaction equation:

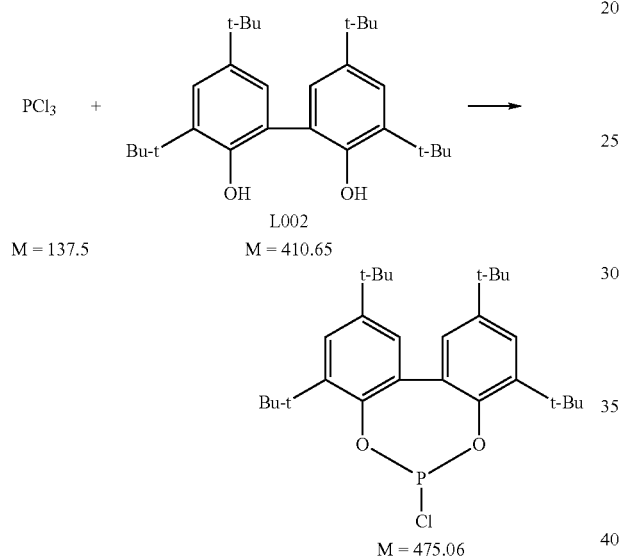

The following experiment was carried out using the protective gas technique. 41.1 g (0.1 mol) of bisphenyl compound L002 were weighed into a secured 500 ml Schlenk vessel. The filled Schlenk vessel was subsequently evacuated and argon was admitted. While stirring, 200 ml of dried toluene and, by means of a syringe which had previously been flushed with argon, 33.4 g (0.33 mol)=46 ml of dried triethylamine were added and dissolved. To dissolve the bisphenyl compound, slight warming (by means of the hand) may be necessary.

200 ml of dried toluene were placed in a secured 1 l Schlenk vessel and 13.8 g (0.1 mol)=8.8 ml of phosphorus trichloride (added by means of a syringe flushed with argon) were dissolved therein. The previously prepared diol/toluene/triethylamine mixture was siphoned dropwise into this solution while stirring at a temperature of from −5 to 0° C. Should ammonium chloride precipitate and make stirring of the mixture difficult, additional solvent can be added at this point. The reaction mixture was then allowed to warm to room temperature by being left to stand overnight. The ammonium chloride obtained was subsequently filtered off by means of a frit and the filtercake was washed with 2×50 ml of dried toluene.

For the further work-up, the solvent was distilled off from the filtrate at room temperature in an oil pump vacuum using cold traps cooled by means of liquid nitrogen. The chlorophosphite obtained was analyzed and stored in a glove box. The yield was about 90% and the purity, determined by GC/MS, was >99% by mass.

Example 1.3

Preparation of ligand L037_01 by reaction of chlorophosphite (L008_01) with 2,2'-bis(3,5-di-tert-butyl)phenol (L002)

Reaction equation:

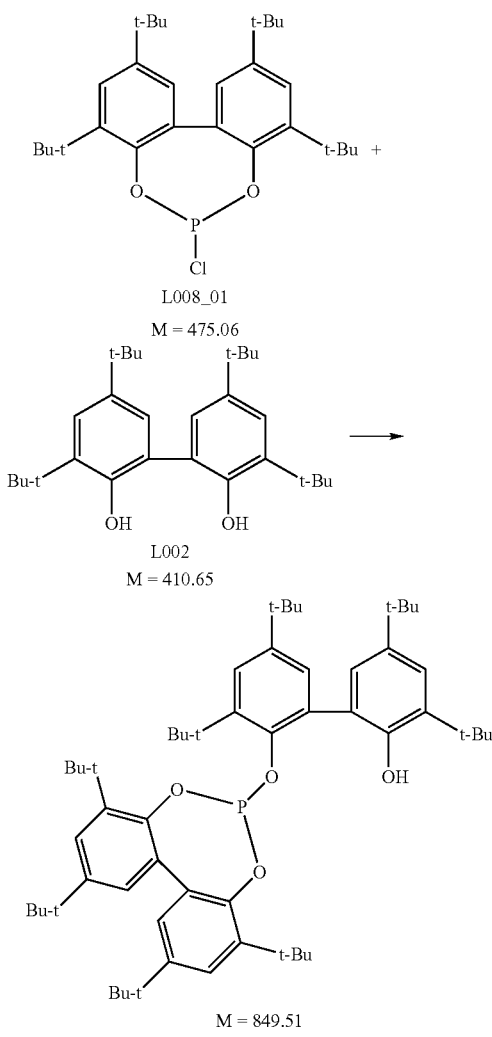

The following experiment was carried out using the protective gas technique. 41.1 g (0.1 mol) of the bisphenyl compound L002 were weighed into a secured 1 l Schlenk vessel. The Schlenk vessel was subsequently evacuated and argon was admitted. 350 ml of dried toluene and, by means of a syringe which had previously been flushed with argon, 12.2 g (0.12 mol)=16.8 ml of dried triethylamine were then added and dissolved with vigorous stirring. To dissolve the bisphenyl compound, slight warming (by means of the hand) may be necessary.

47.5 g (0.1 mol) of chlorophosphite L008_01 were subsequently weighed into a secured 250 ml Schlenk vessel under protective gas in a glove box. 200 ml of dried toluene were subsequently introduced into the Schlenk vessel and the salt was dissolved with stirring. The solution obtained was siphoned dropwise into the diol/toluene/triethylamine solution at a temperature of about −10° C. The reaction mixture was then allowed to warm to room temperature by being allowed to stand overnight. The mixture was then heated to 80° C. and maintained at this temperature for 1 hour. To test for complete conversion, ammonium chloride was allowed to settle and a GC/MS analysis was carried out on the supernatant solution. If the analysis indicated that the starting materials had not yet reacted completely, heating was continued at 80° C. for 1 hour. The test for starting material by means of GC/MS was subsequently carried out as before and the procedure was repeated again if necessary. The precipitated ammonium chloride was subsequently filtered off on a frit and the filtercake was washed with 2×50 ml of dried toluene.

For the further work-up, the solvent was distilled off from the filtrate at room temperature in an oil pump vacuum using cold traps cooled by means of liquid nitrogen. The crude product obtained was washed with about 500 ml of dried acetonitrile. The purified salt was separated off by filtration on a frit, washed twice with 50 ml of dried acetonitrile, dried, analyzed and stored in a glove box. The yield was about 70% and the purity, determined by means of $^{31}$P-NMR, was >97% by mass.

Example 1.4

Preparation of ligand L062__01 by reaction of 1-hydroxy-2-naphthoic acid with phosphorus trichloride to form chloronaphthyldioxaphosphorinone Reaction equation:

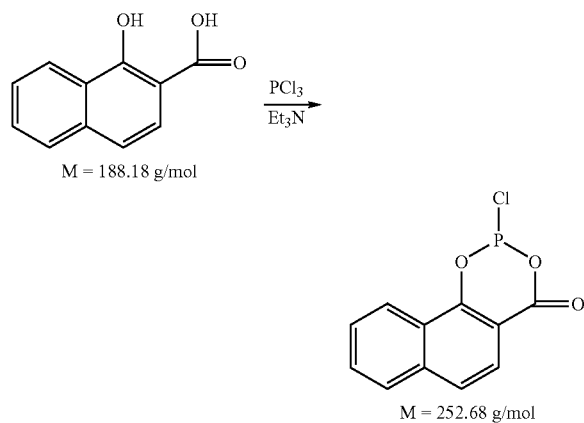

The experiment described below was carried out using the protective gas technique. 18.9 g (0.1 mol) of 1-hydroxy-2-naphthoic acid were weighed into a secured 500 ml Schlenk vessel. The Schlenk vessel was subsequently evacuated, heated to hand heat by means of a hair dryer and, after cooling, argon was admitted. 250 ml of dried toluene were then siphoned in and the mixture was stirred vigorously.

100 ml of dried toluene were placed in a second secured 250 ml Schlenk vessel. 30.7 g (0.3 mol)=42.2 ml of triethylamine and 13.9 g (0.1 mol)=8.8 ml of phosphorus trichloride were subsequently introduced by means of a syringe which had been flushed with argon while stirring. The solution obtained was siphoned a little at a time into the naphthoic acid solution at room temperature over a period of 1.5 hours while stirring vigorously. During this addition, the acid slowly dissolved and insoluble ammonium chloride was formed (suspension reaction). The reaction mixture was subsequently stirred until the following morning.

The conversion test carried out at this point in example 1.3 could not be carried out since the large amount of ammonium chloride had not settled properly. The ammonium chloride was then firstly filtered off on a frit and washed twice with 100 ml of dried toluene. GC/MS was subsequently carried out on the filtrate obtained in order to check the conversion.

To determine the mass of chlorophosphite, all of the toluene was separated off by means of an oil pump vacuum at room temperature using cold traps filled with liquid nitrogen and the product which remained was weighed. For further processing, the defined amount of chlorophosphite was dissolved with stirring in 300 ml of dried toluene and was stored in a refrigerator until used further. The yield was about 90% and the purity determined by means of GC/MS was >99% by mass.

Example 1.5

Preparation of ligand IX by reaction of diorgano phosphite hydroxide (L037__01) with chloronaphthyldioxaphosphorinone (L062__01)

Reaction equation:

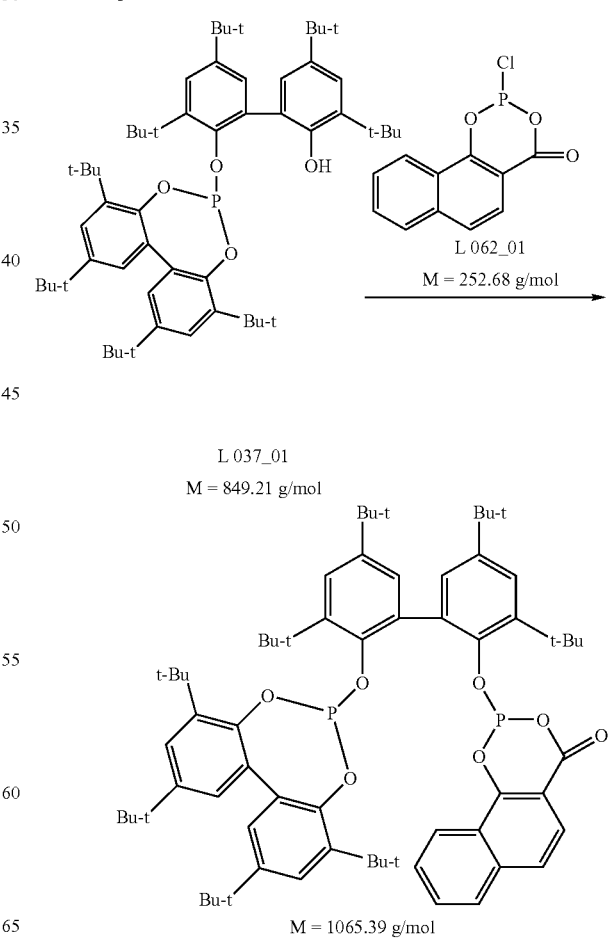

The experiment described below was carried out using the protective gas technique. 42.5 g (0.05 mol) of diorgano phosphite hydroxide L037_01 were weighed into a secured 500 ml Schlenk vessel. 200 ml of dried toluene and, by means of a syringe which had been flushed with argon, 11.2 g (0.11 mol)=15.5 ml of triethylamine were subsequently added and dissolved with stirring. This solution was siphoned dropwise while stirring vigorously into a secured 1000 ml Schlenk vessel containing the calculated, measured amount of starting solution of L062_01 from example 1.4 [0.06 mol (with a slight excess of chlorophosphite)] at a temperature of 0-4° C. The reaction solution was subsequently allowed to warm to room temperature overnight. On the next morning, the ammonium chloride formed was allowed to settle and a sample for GC/MS was taken from the supernatant solution [test for conversion of starting material (fragment L037_01)] if the starting materials had not yet reacted completely, the mixture was heated at 60° C. for 2 hours. A test for the presence of starting material was subsequently carried out as before by means of GC/MS. The ammonium chloride formed was then filtered off on a frit and the filtercake was washed with 2×50 ml of dried toluene.

For the work-up, the solvent was distilled off from the filtrate at room temperature by means of an oil pump vacuum using cold traps filled with liquid nitrogen. The crude product obtained was washed with about 400 ml of dried acetonitrile. The washings were separated off by means of frits and the purified salt was washed with 2×50 ml of dried acetonitrile, dried, analyzed and stored in a glove box. The yield was about 70% and the purity, determined by means of $^{31}$P-NMR, was >99% by mass.

Example 2

Hydroformylation Experiments

The effectiveness of the stabilizers was tested by means of repeated autoclave experiments. The procedure was as follows:

The experiments were carried out in 300 ml autoclaves. The autoclaves were electrically heated and could be operated at a temperature of up to about 150° C. The pressure was kept constant by means of Bronkhorst pressure regulators. The autoclaves could be operated at a pressure of up to 6 MPa. The autoclaves were additionally equipped with a stirrer and a sampling facility.

In examples 2.1 to 2.4, about 23 mg of rhodium nonanoate and 0.31 g of ligand IX (from example 1) together with about 75 g of tetrabutane were in each case placed in the autoclave.

The stabilizer was placed in the autoclave in a significant molar excess over rhodium (about 10- to 20-fold excess).

The catalyst was preactivated under synthesis gas at 120° C. and 5 bar for about 2.5 hours, and the pressure was then set to 2 MPa and about 75 g of 1-octene were added via a heatable pressure bomb. The hydroformylation ran for 2 hours. The reaction mixture was then depressurized, cooled to room temperature, blanketed with argon and fed into the top of a falling film evaporator. The falling film evaporator was operated at 18 hPa and 120° C. Under these conditions, the aldehydes were separated off. The catalyst solution was obtained at the bottom of the falling film evaporator and, after being supplemented by the amount of solvent lost, was recirculated to the autoclave for the next run. The number of cycles achieved before the conversion of the olefin decreased was a measure of the effectiveness of the stabilizer.

Example 2.1

Comparative Experiment: Hydroformylation without Stabilizer (Experiment 1104)

The experiment in example 2.1 was carried out as described in example 2. The conversion dropped to 14.24% in only the 2nd cycle.

TABLE 1

| | | Experimental results in example 2.1 | | | | | |
|---|---|---|---|---|---|---|---|
| Experiment No. | Cycle No. | Amount of solvent added [g] | Extra amount of solvent [g] | Amount of olefin added [g] | Olefin conversion [%] | Alcohols, total [%] | Octane, total [%] |
| 1104_0 | 0 | 75.967 | — | 76.2733 | 80.54 | 0.27 | 0.61 |
| 1104_1 | 1 | 84.7757 | — | 72.5452 | 70.17 | 0.26 | 0.60 |
| 1104_2 | 2 | 81.3123 | — | 74.8923 | 14.25 | 0.13 | 0.18 |

Example 2.2

According to the Invention: Hydroformylation using the stabilizer bis(2,2,6,6-tetramethylpiperidyl) sebacate (experiment 1126)

In this experiment, 0.5475 g of stabilizer (stabilizer bis(2,2,6,6-tetramethylpiperidyl) sebacate) were added. The evaporator temperature was 125° C. Otherwise, all conditions were set as in example 2.1. The following results were obtained: 14 cycles were achieved. The conversion dropped from 79% to about 29%. Aldolization, hydrogenation to the alcohol and hydrogenation of the olefin played virtually no role. The results based on the individual cycles are shown in table 2.

TABLE 2

Experimental results for example 2.2

| Experiment No. | Cycle No. | Amount of solvent added [g] | Extra amount of solvent [g] | Amount of olefin added [g] | Olefin conversion [%] | C9-aldols [%] | Alcohols, total [%] | Octane total [%] |
|---|---|---|---|---|---|---|---|---|
| 1126_0 | 0 | 75.0918 | — | 75.2366 | 78.89 | 0.05 | 0.32 | 0.54 |
| 1126_1 | 1 | 79.5048 | — | 75.3371 | 75.66 | 0.06 | 0.25 | 0.52 |
| 1126_2 | 2 | 77.1771 | — | 74.5512 | 78.84 | 0.08 | 0.24 | 0.51 |
| 1126_3 | 3 | 75.0533 | 6.0473 | 74.5690 | 77.88 | 0.08 | 0.22 | 0.55 |
| 1126_4 | 4 | 75.0343 | 10.1164 | 75.1531 | 78.06 | 0.10 | 0.22 | 0.55 |
| 1126_5 | 5 | 75.2238 | 11.5470 | 74.6837 | 75.70 | 0.13 | 0.25 | 0.55 |
| 1126_6 | 6 | 75.3281 | 7.1432 | 74.4918 | 72.55 | 0.08 | 0.25 | 0.48 |
| 1126_7 | 7 | 75.1029 | 4.9285 | 75.8905 | 70.91 | 0.11 | 0.29 | 0.47 |
| 1126_8 | 8 | 75.2798 | 8.2135 | 75.9723 | 65.65 | 0.08 | 0.23 | 0.39 |
| 1126_9 | 9 | 73.9801 | 9.6182 | 74.5358 | 62.50 | 0.11 | 0.26 | 0.38 |
| 1126_10 | 10 | 75.2252 | 5.6061 | 74.5663 | 59.20 | 0.11 | 0.29 | 0.32 |
| 1126_11 | 11 | 75.1119 | 13.6492 | 75.3301 | 55.27 | 0.15 | 0.29 | 0.36 |
| 1126_12 | 12 | 75.3528 | 5.8548 | 76.2046 | 51.37 | 0.09 | 0.19 | 0.31 |
| 1126_13 | 13 | 75.3545 | 3.3502 | 75.5026 | 39.68 | 0.13 | 0.18 | 0.27 |
| 1126_14 | 14 | 75.5317 | 10.9327 | 75.4594 | 29.41 | 0.12 | 0.31 | 0.31 |

Example 2.3

According to the Invention: Experiment 1127

The experiment was carried out in a manner identical to example 2.2, except that the evaporator temperature was increased to 130° C. The results are shown in table 3. Once again, 14 cycles were achieved. The conversion dropped from 82.9% to 38.0%. Here too, aldolization, hydrogenation of the aldehyde to the alcohol and hydrogenation of the olefin to the alkane played no role.

Example 2.4

According to the Invention: Experiment 1128

The experiment was carried out in a manner identical to example 2.3, except that the evaporator temperature was increased to 140° C. The results are shown in table 4. 12 cycles were achieved. The conversion dropped from 73.1% to 39.2%. Here too, aldolization, hydrogenation of the aldehyde to the alcohol and hydrogenation of the olefin to the alkane played no role.

TABLE 3

Experimental results for example 2.3

| Experiment No. | Cycle No. | Amount of solvent added [g] | Extra amount of solvent [g] | Amount of olefin added [g] | Olefin conversion [%] | C9-aldols [%] | Alcohols, total [%] | Octane total [%] |
|---|---|---|---|---|---|---|---|---|
| 1127_0 | 0 | 75.7973 | — | 74.8506 | 82.94 | 0.03 | 0.27 | 0.53 |
| 1127_1 | 1 | 81.7284 | — | 74.5348 | 79.65 | 0.03 | 0.23 | 0.49 |
| 1127_2 | 2 | 74.9832 | 8.4589 | 75.5243 | 78.72 | 0.03 | 0.23 | 0.47 |
| 1127_3 | 3 | 75.853 | 11.9701 | 74.1994 | 74.86 | 0.05 | 0.26 | 0.49 |
| 1127_4 | 4 | 75.7285 | 11.0764 | 75.6125 | 73.1 | 0.06 | 0.26 | 0.4 |
| 1127_5 | 5 | 75.2402 | 12.8193 | 74.8118 | 68.71 | 0.15 | 0.24 | 0.43 |
| 1127_6 | 6 | 74.3849 | 8.2825 | 75.2589 | 67.78 | 0.24 | 0.35 | 0.42 |
| 1127_7 | 7 | 74.8802 | 8.7427 | 75.7335 | 63.33 | 0.08 | 0.34 | 0.5 |
| 1127_8 | 8 | 74.9298 | 12.056 | 74.9144 | 66.79 | 0.16 | 0.34 | 0.46 |
| 1127_9 | 9 | 75.0866 | 6.0483 | 74.6021 | 59.03 | 0.17 | 0.27 | 0.45 |
| 1127_10 | 10 | 93.6196 | — | 75.2969 | 63.65 | 0.22 | 0.07 | 0.35 |
| 1127_11 | 11 | 75.5993 | 12.8816 | 75.8578 | 56.86 | 0.15 | 0.2 | 0.3 |
| 1127_12 | 12 | 74.2646 | 9.3892 | 75.2502 | 54.54 | 0.33 | 0.18 | 0.33 |
| 1127_13 | 13 | 75.0734 | 10.4896 | 74.308 | 45.21 | 0.32 | 0.21 | 0.31 |
| 1127_14 | 14 | 75.2771 | 8.7704 | 75.3358 | 37.96 | 0.29 | 0.27 | 0.29 |

TABLE 4

Experimental results for example 2.4

| Experiment No. | Cycle No. | Amount of solvent added [g] | Extra amount of solvent [g] | Amount of olefin added [g] | Olefin conversion [%] | C9-aldols [%] | Alcohols, total [%] | Octane total [%] |
|---|---|---|---|---|---|---|---|---|
| 1128_0 | 0 | 74.6361 | — | 75.0034 | 73.08 | 0.01 | 0.30 | 0.51 |
| 1128_1 | 1 | 74.7814 | 14.2622 | 74.7096 | 71.49 | 0.02 | 0.31 | 0.54 |
| 1128_2 | 2 | 75.8779 | 10.6546 | 75.0561 | 71.19 | 0.07 | 0.30 | 0.55 |
| 1128_3 | 3 | 76.3051 | 17.2818 | 75.2654 | 69.92 | 0.06 | 0.30 | 0.51 |
| 1128_4 | 4 | 74.5929 | 8.7161 | 74.4077 | 71.75 | 0.07 | 0.36 | 0.53 |
| 1128_5 | 5 | 74.1238 | 10.1064 | 74.8612 | 66.89 | 0.12 | 0.32 | 0.62 |
| 1128_6 | 6 | 75.2458 | 15.9996 | 76.7338 | 65.67 | 0.00 | 0.10 | 0.86 |
| 1128_7 | 7 | 75.2060 | 8.8916 | 76.0116 | 63.92 | 0.12 | 0.34 | 0.62 |
| 1128_8 | 8 | 74.8598 | 13.8460 | 75.1726 | 64.82 | 0.12 | 0.30 | 0.44 |
| 1128_9 | 9 | 75.0888 | 12.5753 | 74.6343 | 59.39 | 0.15 | 0.33 | 0.38 |
| 1128_10 | 10 | 75.1516 | 11.6306 | 74.4768 | 56.59 | 0.15 | 0.26 | 0.33 |
| 1128_11 | 11 | 75.1347 | 9.1005 | 74.8443 | 56.21 | 0.35 | 0.34 | 0.35 |
| 1128_12 | 12 | 75.5075 | 15.1794 | 75.2163 | 39.16 | 0.18 | 0.30 | 0.36 |

The examples thus demonstrate the stabilizing effect of the sterically hindered secondary amine of the formula I on the catalyst system, and at the same time show that the stabilizer has no adverse effects on the aldolization of the aldehyde.

The invention claimed is:

1. A carbonylation process in which at least one compound which is capable of being carbonylated by a carbon monoxide is reacted with the carbon monoxide in the presence of a metal complex catalyst of a metal of transition group VIII of the Periodic Table of the Elements which has an organophosphorus compound as ligand, wherein the carbonylation is carried out in the presence of a sterically hindered secondary amine having the general structural formula I

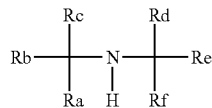

I where Ra, Rb, Rc, Rd, Re and Rf are identical or different hydrocarbon radicals which may be joined to one another.

2. The process as claimed in claim 1, wherein an amine having a 2,2,6,6-tetramethylpiperidine unit II

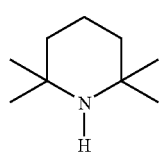

II is used as secondary amine.

3. The process as claimed in claim 1, wherein at least one of the compounds of the structural formulae IIb to IIg

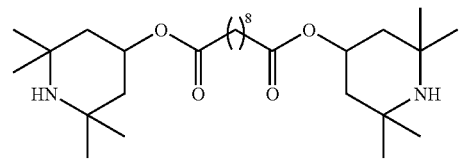

IIb

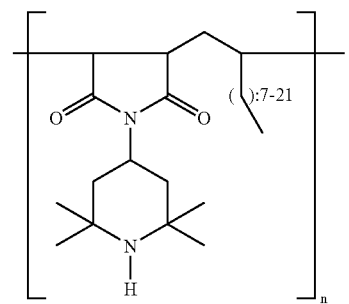

IIc where n=1 to 20

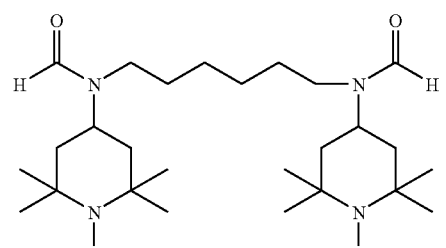

IId

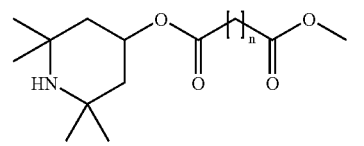

IIe where n=1 to 12

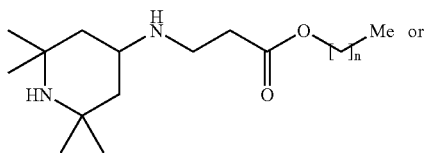

IIf where n=1 to 17

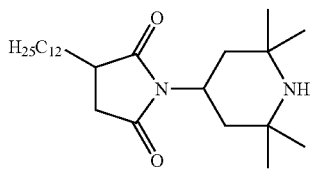

IIg is used as secondary amine.

4. The process as claimed in claim 1, wherein at least one compound having two or more of the functional groups of the formulae III to VI or at least one compound of one of the formulae III to VI $PR^2R^3R^4$      III $PR^2R^3(TR^5)$      IV $PR^2(TR^5)(TR^6)$      V $P(TR^5)(TR^6)(TR^7)$      VI where T=O, NH or $NR^8$ and $R^2$ to $R^8$ are identical or different organic radicals which have from 1 to 50 carbon atoms and may be joined to one another via a covalent bond, is used as organophosphorus ligand.

5. The process as claimed in claim 4, wherein at least one compound of the formula VIIc-9, VIIc-10 or VIIc-11

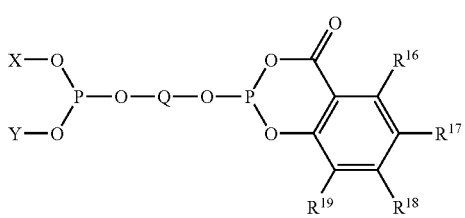

VIIc-9

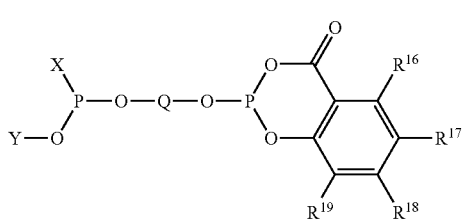

VIIc-10

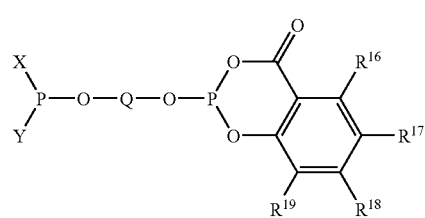

VIIc-11 where X and Y are substituted or unsubstituted, aliphatic, alicyclic, aliphatic-alicyclic, heterocyclic, aliphatic-heterocyclic, aromatic-aromatic or aliphatic-aromatic hydrocarbon radicals having from 1 to 50 carbon atoms, with X and Y being identical or different or being covalently bound to one another, and Q is an at least divalent, substituted or unsubstituted aliphatic, alicyclic, aliphatic-alicyclic, heterocyclic, aliphatic-heterocyclic, aromatic, aromatic-aromatic or aliphatic-aromatic hydrocarbon radical preferably having from 1 to 50 carbon atoms, with substituted hydrocarbon radicals having substituents selected from among $-N(R^{20})_2$, $-NHR^{20}$, $-NH_2$, fluorine, chlorine, bromine, iodine, $-OH$, $-CN$, $-C(O)-R^{20}$, $-C(O)H$ or $-C(O)O-R^{20}$, $-CF_3$, $-O-R^{20}$, $-C(O)N-R^{20}$, $-OC(O)-R^{20}$ and/or $-Si(R^{20})_3$, where $R^{20}$ is a monovalent hydrocarbon radical which preferably has from 1 to 20 carbon atoms and if a plurality of hydrocarbon radicals $R^{20}$ are present, these can be identical or different, and $R^{16}$ to $R^{19}$ are selected independently from among monovalent substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having 1 to 50 carbon atoms, H, F, Cl, Br, I, $-CF_3$, $-CH_2(CF_2)_jCF_3$ where j=0-9, $-OR^{21}$, $-COR^{21}$, $-CO_2R^{21}$, $-CO_2M$, $-SR^{21}$, $-SO_2R^{21}$, $-SOR^{21}$, $-SO_3R^{21}$, $-SO_3M$, $-SO_2NR^{21}R^{22}$, $-NR^{21}R^{22}$, $-N=CR^{21}R^{22}$, where $R^{21}$ and $R^{22}$ are selected independently from among H, monovalent substituted or unsubstituted aliphatic and aromatic hydrocarbon radicals having from 1 to 25 carbon atoms and M is an alkali metal ion, formally half an alkaline earth metal, ammonium or phosphonium ion, or adjacent radicals $R^{16}$ to $R^{19}$ together form a fused substituted or unsubstituted aromatic, heteroaromatic, aliphatic, mixed aromatic-aliphatic or mixed heteroaromatic-aliphatic ring system; with substituted hydrocarbon radicals having substituents selected from among $-N(R^{23})_2$, $-NHR^{23}$, $-NH_2$, fluorine, chlorine, bromine, iodine, $-OH$, $-CN$, $-C(O)-R^{23}$, $-C(O)H$ or $-C(O)O-R^{23}$, $-CF_3$, $-O-R^{23}$, $-C(O)N-R^{23}$, $-OC(O)-R^{23}$ and/or $-Si(R^{23})_3$, where $R^{18}$ is a monovalent hydrocarbon radical which preferably has from 1 to 20 carbon atoms and when a plurality of hydrocarbon radicals $R^{23}$ are present, these can be identical or different, and the radicals $R^{16}$, $R^{17}$, $R^{18}$ and $R^{19}$ are identical or different, is used as organophosphorus ligand.

6. The process as claimed in claim 4, wherein a compound of the formula VIIb-1 or VIIb-2

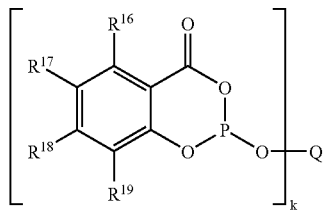
VIIb-1

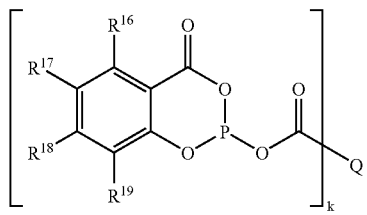
VIIb-2 where k=2 and $R^{16}$, $R^{17}$, $R^{18}$, and $R^{19}$ having the meanings given for the formulae VIIc-9 to VIIc-11, Q is a divalent substituted or unsubstituted aliphatic, alicyclic, mixed aliphatic-alicyclic, heterocyclic, mixed aliphatic-heterocyclic, aromatic, heteroaromatic, mixed aliphatic-aromatic hydrocarbon radical having from 1 to 50 carbon atoms, with aliphatic parts of Q being able to contain oxygen, sulfur and/or nitrogen and substituted hydrocarbon radicals Q being able to have substituents having the same meanings as $R^{16}$ to $R^{19}$, is used as organophosphorus ligand.

7. The process as claimed in claim 1, wherein the organophosphorus ligand is used in a molar ratio to the metal at which the organophosphorus ligand is also present as free ligand in the reaction mixture.

8. The process as claimed in claim 1, wherein at least one olefinically unsaturated compound selected from the group consisting of substituted or unsubstituted alpha-olefins, internal olefins, cycloolefins, alkenyl alkyl ethers and alkenols is used as starting compound to be carbonylated.

9. The process as claimed in claim 1, wherein at least one compound selected from the group consisting of among hydrogen, water, amine and alcohol is used as further reactant in addition to the carbon monoxide and the starting compound to be carbonylated.

10. The process as claimed in claim 1, wherein at least hydrogen is used as further reactant in addition to the carbon monoxide and the starting compound to be carbonylated and a hydroformylation is carried out.

11. The process as claimed in claim 1, wherein cobalt or rhodium is used as the metal of transition group VIII of the Periodic Table.

12. The process as claimed in claim 1, wherein the sterically hindered secondary amine is used in a molar ratio to the catalyst metal of from 0.1:1 to 100:1 in the reaction mixture.

13. A mixture comprising a metal complex catalyst of a metal of transition group VIII of the Periodic Table of the Elements which has an organophosphorus compound as a ligand and a sterically hindered secondary amine having the formula I,

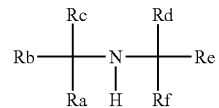
I where Ra, Rb, Rc, Rd, Re and Rf are identical or different hydrocarbon radicals which may be joined to one another.

14. The mixture as claimed in claim 13, wherein an amine having a 2,2,6,6-tetramethylpiperidine unit II

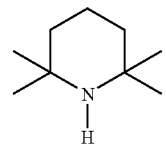
II is present as secondary amine.

15. The mixture as claimed in claim 13, wherein at least one compound selected from among the compounds of the formulae IIb to IIg

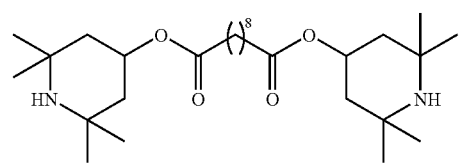
IIb

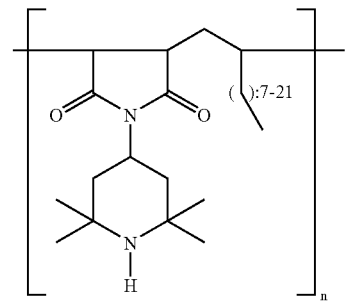
IIc where n=1 to 20

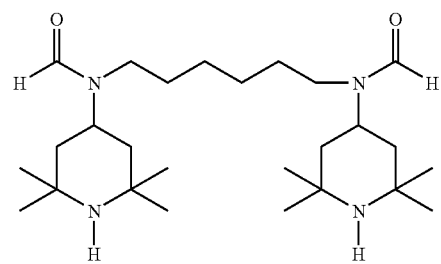
IId

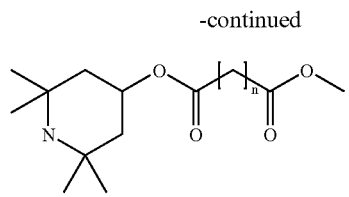

where n=1 to 12

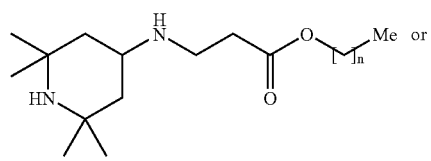

where n=1 to 17

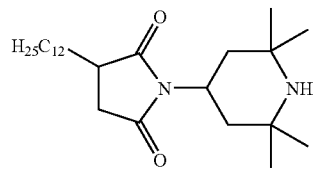

is present as secondary amine.

16. The mixture as claimed in claim 13, comprising at least one compound having two or more of the functional groups of the formulae III to VI or at least one compound of one of the formulae III to VI $PR^2R^3R^4$   III $PR^2R^3(TR^5)$   IV $PR^2(TR^5)(TR^6)$   V $P(TR^5)(TR^6)(TR^7)$   VI where T=O, NH or $NR^8$ and $R^2$ to $R^8$ are identical or different organic radicals which have from 1 to 50 carbon atoms and are optionally joined to one another via a covalent bond, as an organophosphorus ligand.

17. The mixture as claimed in claim 13 which comprises at least one compound of the formula VIIc-9, VIIc-10 or VIIc-11

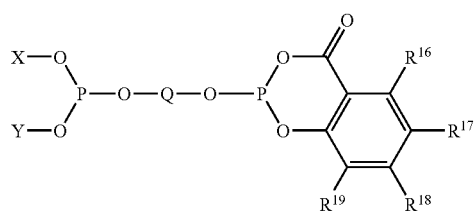

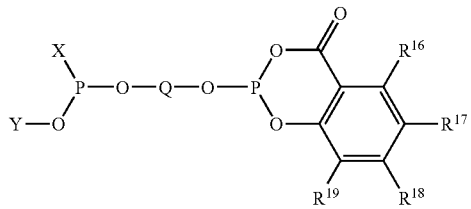

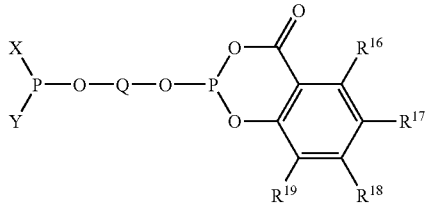

where X and Y are substituted or unsubstituted, aliphatic, alicyclic, aliphatic-alicyclic, heterocyclic, aliphatic-heterocyclic, aromatic-aromatic or aliphatic-aromatic hydrocarbon radicals having from 1 to 50 carbon atoms, with X and Y being identical or different or being covalently bound to one another, and Q is an at least divalent, substituted or unsubstituted aliphatic, alicyclic, aliphatic-alicyclic, heterocyclic, aliphatic-heterocyclic, aromatic, aromatic-aromatic or aliphatic-aromatic hydrocarbon radical preferably having from 1 to 50 carbon atoms, with substituted hydrocarbon radicals having substituents selected from among —$N(R^{20})_2$, —$NHR^{20}$, —$NH_2$, fluorine, chlorine, bromine, iodine, —OH, —CN, —C(O)—$R^{20}$, —C(O)H or —C(O)O—$R^{20}$, —$CF_3$, —O—$R^{20}$, —C(O)N—$R^{20}$, —OC(O)—$R^{20}$ and/or —$Si(R^{20})_3$, where $R^{20}$ is a monovalent hydrocarbon radical which preferably has from 1 to 20 carbon atoms and if a plurality of hydrocarbon radicals $R^{20}$ are present, these can be identical or different, and $R^{16}$ to $R^{19}$ are selected independently from among monovalent substituted or unsubstituted aliphatic, alicyclic, aromatic, heteroaromatic, mixed aliphatic-alicyclic, mixed aliphatic-aromatic, heterocyclic, mixed aliphatic-heterocyclic hydrocarbon radicals having 1 to 50 carbon atoms, H, F, Cl, Br, I, —$CF_3$, —$CH_2(CF_2)_jCF_3$ where j=0-9, —$OR^{21}$, —$COR^{21}$, —$CO_2R^{21}$, —$CO_2M$, —$SR^{21}$, —$SO_2R^{21}$, —$SOR^{21}$, —$SO_3R^{21}$, —$SO_3M$, —$SO_2NR^{21}R^{22}$, —$NR^{21}R^{22}$, —N=$CR^{21}R^{22}$, where $R^{21}$ and $R^{22}$ are selected independently from among H, monovalent substituted or unsubstituted aliphatic and aromatic hydrocarbon radicals having from 1 to 25 carbon atoms and M is an alkali metal ion, formally half an alkaline earth metal, ammonium or phosphonium ion, or adjacent radicals $R^{16}$ to $R^{19}$ together form a fused substituted or unsubstituted aromatic, heteroaromatic, aliphatic, mixed aromatic-aliphatic or mixed heteroaromatic-aliphatic ring system; with substituted hydrocarbon radicals having substituents selected from among —$N(R^{23})_2$, —$NHR^{23}$, —$NH_2$, fluorine, chlorine, bromine, iodine, —OH, —CN, —C(O)—$R^{23}$, —C(O)H or —C(O)O—$R^{23}$, —$CF_3$, —O—$R^{23}$, —C(O)N—$R^{23}$, —OC(O)—$R^{23}$ and/or —$Si(R^{23})_3$, where $R^{18}$ is a monovalent hydrocarbon radical which preferably has from 1 to 20 carbon atoms and when a plurality of hydrocarbon radicals $R^{23}$ are present, these can be identical or different, and the radicals $R^{16}$, $R^{17}$, $R^{18}$ and $R^{19}$ are identical or different, as an organophosphorus ligand.

18. The mixture as claimed in claim 13 which comprises a compound of the formula VIIb-1 or VIIb-2

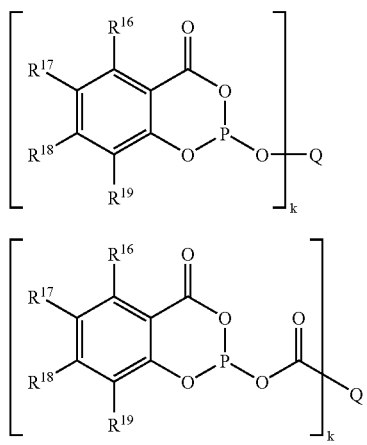

where k=2 and $R^{16}$, $R^{17}$, $R^{18}$, and $R^{19}$ having the meanings given for the formulae VIIc-9 to VIIc-11, Q is a divalent substituted or unsubstituted aliphatic, alicyclic, mixed aliphatic-alicyclic, heterocyclic, mixed aliphatic-heterocyclic, aromatic, heteroaromatic, mixed aliphatic-aromatic hydrocarbon radical having from 1 to 50 carbon atoms, with aliphatic parts of Q being able to contain oxygen, sulfur and/or nitrogen and substituted hydrocarbon radicals Q being able to have substituents having the same meanings as $R^{16}$ to $R^{19}$, as an organophosphorus ligand.

19. The mixture as claimed in claim 13, wherein the organophosphorus ligand is present in a molar ratio to the metal of from 0.1:1 to 100:1.

20. The mixture as claimed in claim 13, wherein cobalt or rhodium is present as the metal of transition group VIII of the Periodic Table.

21. The mixture as claimed in claim 13, wherein the stabilizer is present in a molar ratio to the catalyst metal of from 0.1:1 to 100:1.

* * * * *